(12) United States Patent
Arnone et al.

(10) Patent No.: US 8,027,709 B2
(45) Date of Patent: Sep. 27, 2011

(54) RADIATION PROBE AND DETECTING TOOTH DECAY

(75) Inventors: Donald Dominic Arnone, Cambridge (GB); Craig Michael Ciesla, Cambridge (GB)

(73) Assignee: TeraView Limited, Cambridge (GB)

( * ) Notice: Subject to any disclaimer, the term of this patent is extended or adjusted under 35 U.S.C. 154(b) by 1427 days.

(21) Appl. No.: 11/011,703

(22) Filed: Dec. 14, 2004

(65) Prior Publication Data
US 2005/0100866 A1    May 12, 2005

Related U.S. Application Data

(63) Continuation of application No. 10/031,784, filed as application No. PCT/GB00/02849 on Jul. 24, 2000, now abandoned.

(30) Foreign Application Priority Data

Jul. 23, 1999    (GB) .................................. 9917407.0

(51) Int. Cl.
*A61B 5/05* (2006.01)
*A61C 1/00* (2006.01)

(52) U.S. Cl. .......................... 600/407; 600/427; 433/29

(58) Field of Classification Search ................. 433/215, 433/29; 382/128; 600/407, 427, 340, 101–183; 250/341.1; 362/257; 356/241.1; 348/45
See application file for complete search history.

(56) References Cited

U.S. PATENT DOCUMENTS

| | | | | |
|---|---|---|---|---|
| 4,479,499 A * | 10/1984 | Alfano | ........................ | 600/477 |
| 5,710,430 A | 1/1998 | Nuss | ........................ | 250/358.1 |
| 5,769,791 A * | 6/1998 | Benaron et al. | ........................ | 600/473 |
| 5,772,597 A * | 6/1998 | Goldberger et al. | ........................ | 600/473 |
| 5,773,829 A * | 6/1998 | Iwanczyk et al. | ........................ | 250/367 |
| 5,862,287 A | 1/1999 | Stock et al. | ........................ | 385/123 |
| 5,952,818 A * | 9/1999 | Zhang et al. | ........................ | 324/96 |
| 6,201,880 B1 * | 3/2001 | Elbaum et al. | ........................ | 382/100 |
| 6,373,970 B1 * | 4/2002 | Dong et al. | ........................ | 382/128 |
| 2002/0039186 A1 * | 4/2002 | Rosenberg | ........................ | 356/432 |
| 2005/0180620 A1 * | 8/2005 | Takiguchi | ........................ | 382/128 |

FOREIGN PATENT DOCUMENTS

EP    0 438 353    7/1991
(Continued)

OTHER PUBLICATIONS

Hoshi N., et al, "Study on Diagnosis for Tooth Using Millimeter-Waves" IEEE MTT-S International Microwave Symposium Digest, US, New York, NY, IEEE, Jun. 7, 1998, pp. 759-762.

(Continued)

*Primary Examiner* — Cris L Rodriguez
*Assistant Examiner* — Heidi M Eide
(74) *Attorney, Agent, or Firm* — Dickstein Shapiro LLP

(57) ABSTRACT

A probe assembly for examining a sample, the assembly including a probe, a fiber optic cable for communicating signals to and/or from the probe, an emitter for emitting radiation to irradiate the sample and an electro-magnetic radiation detector for detecting radiation which is transmitted or reflected from the sample. The emitter includes a frequency conversion member which emits radiation in response to being irradiated with input radiation which has a different frequency to that of the emitted radiation. At least one of the emitter or detector is located in the probe. The probe is particularly for use as an endoscope or for imaging teeth. The invention also extends to a method of imaging teeth, and apparatus for imaging diseased teeth, for example, teeth with caries or suffering from periodontal disease.

28 Claims, 33 Drawing Sheets

FOREIGN PATENT DOCUMENTS

| EP | 0 828 143 | 3/1998 |
| EP | 0 828 162 | 3/1998 |
| EP | 0 864 298 | 9/1998 |
| EP | 0 864 857 | 9/1998 |
| EP | 0 828 184 | 11/1998 |
| WO | WO 87/00028 | 1/1987 |
| WO | WO 94/20011 | 9/1994 |
| WO | WO 98/52460 | 11/1998 |

OTHER PUBLICATIONS

Arnone D., et al., "Applications of Terahertz (THz) Technology to Medical Imaging", Proceedigs of the SPI-International Society for Optical Engineering, vol. 3828, Jun. 1999, pp. 209-219.

Zhang, X., "Generation and Detection of Pulsed Microwave Signals by THz Optoelectronics", 1997 SMBO/IEEE MTT-S International Microwave and Optoelectronics Conference, "Linking to the Next Century" Proceedings, natal, Brazil, Aug. 11-14, 1997, vol. 1, 1997, pp. 215-220.

Schmitt, J.M., et al., "Optical Determination of Dental Pulp Vitality", IEEE Transactions oon Biomedical Engineering, US, IEEE Inc. New York, vol. 38, No. 4, Apr. 1, 2001, pp. 346-352.

WPI Acc. No. 99-408 143 & JP 11 160 264 A (Lion), Jun. 18, 1999 Abstract.

WPI Acc. No. 98-012 547 & JP 9 276 299 A (Aisin), Oct. 28, 1997, Abstract.

WPI Acc. No. 96-467 699 & JP 8 233 758 A (Lion) Sep. 13, 1996, Abstract.

* cited by examiner

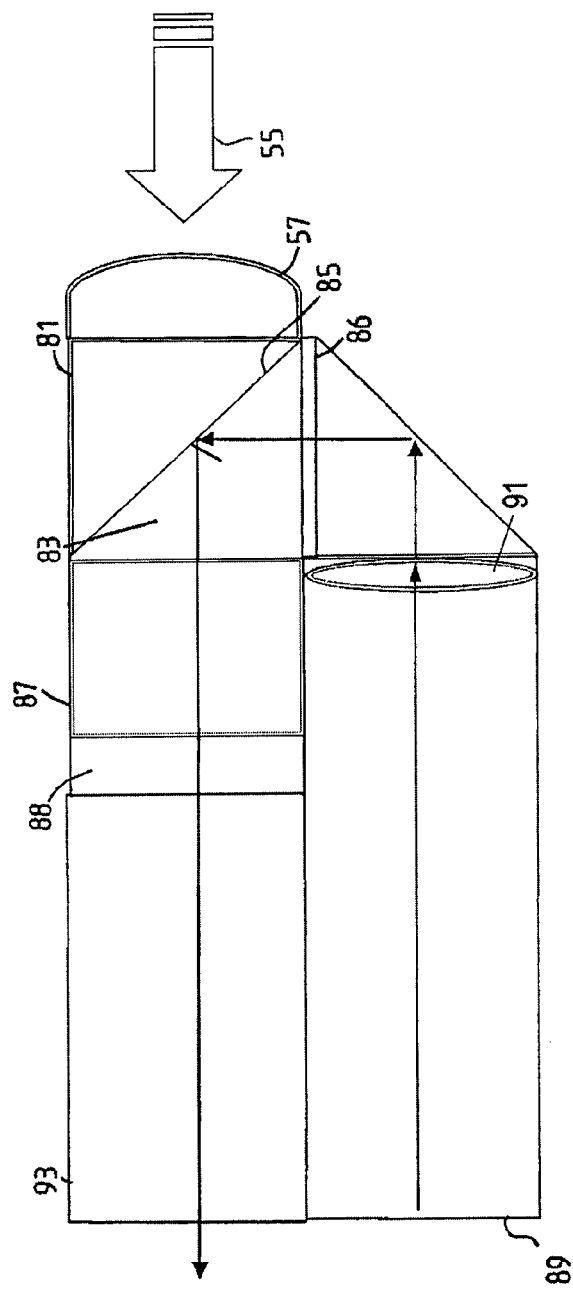

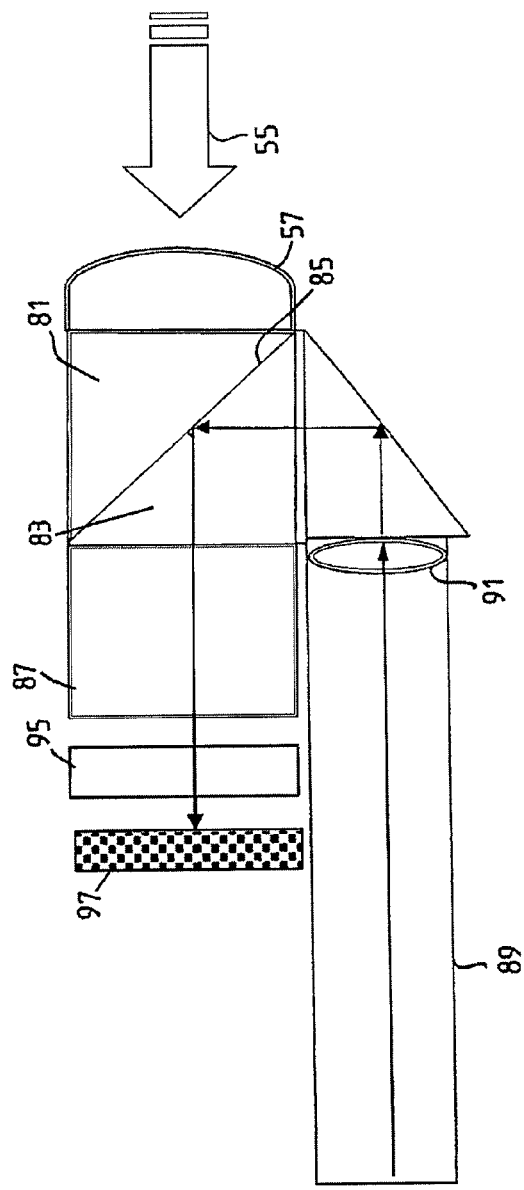

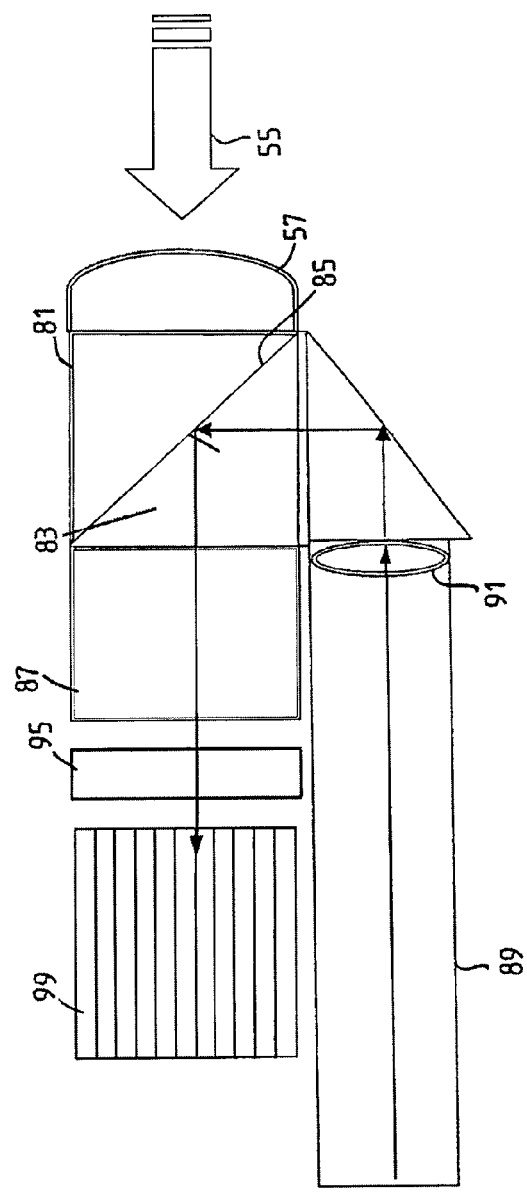

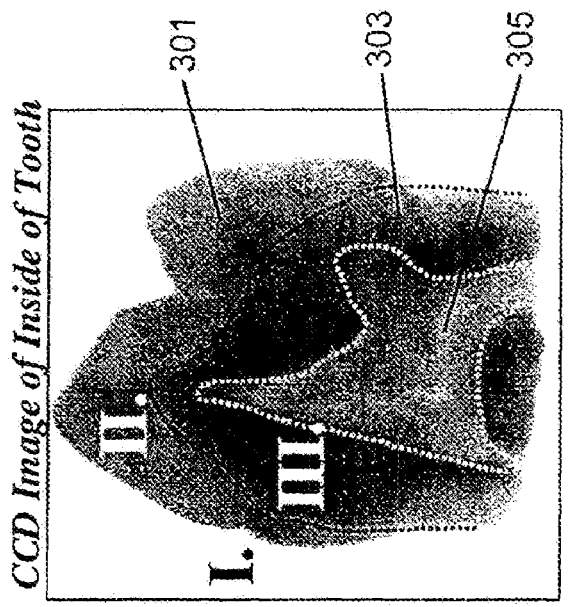
Fig. 23c
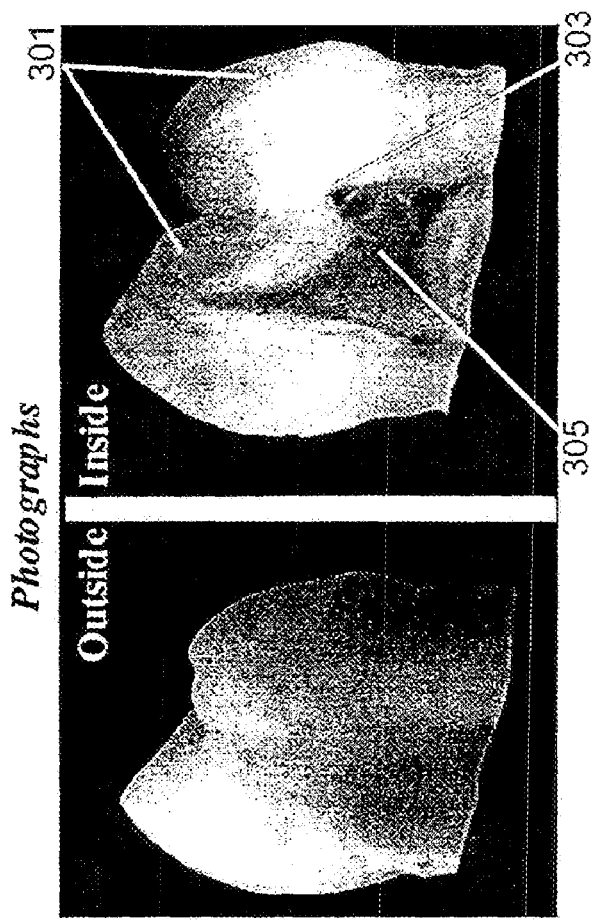
Fig. 23b
Fig. 23a

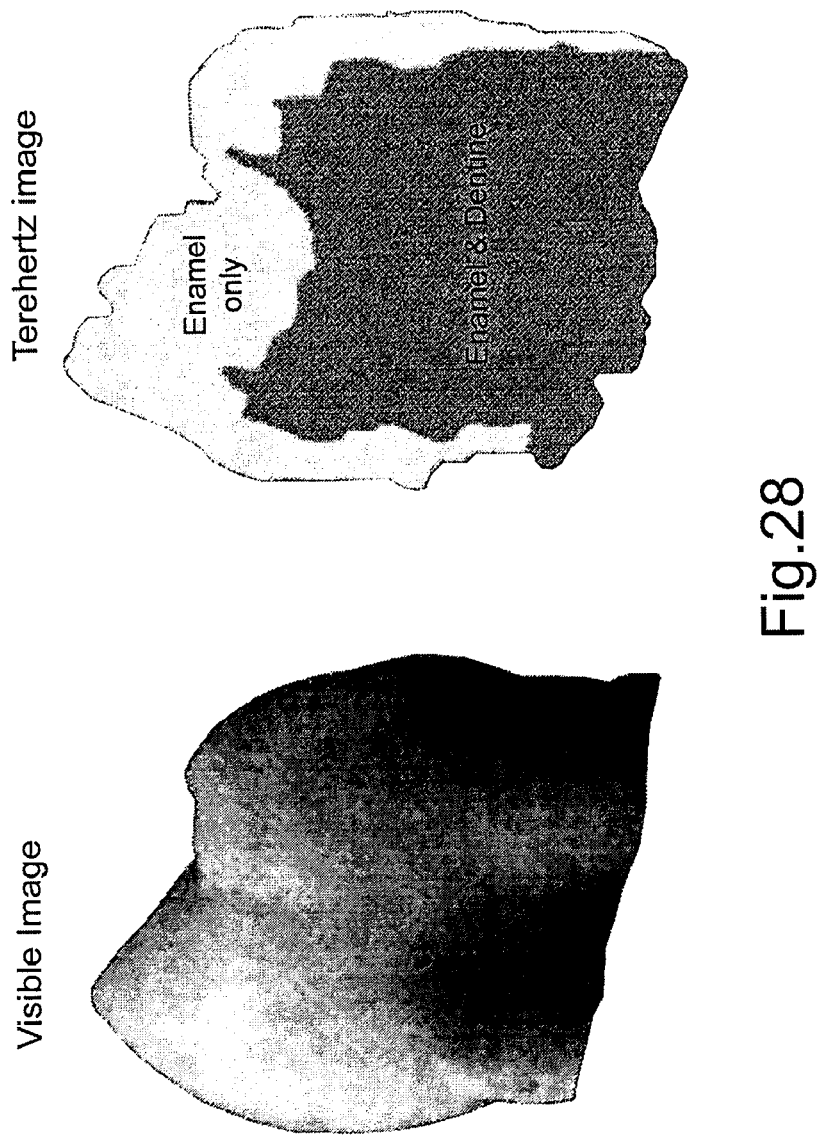

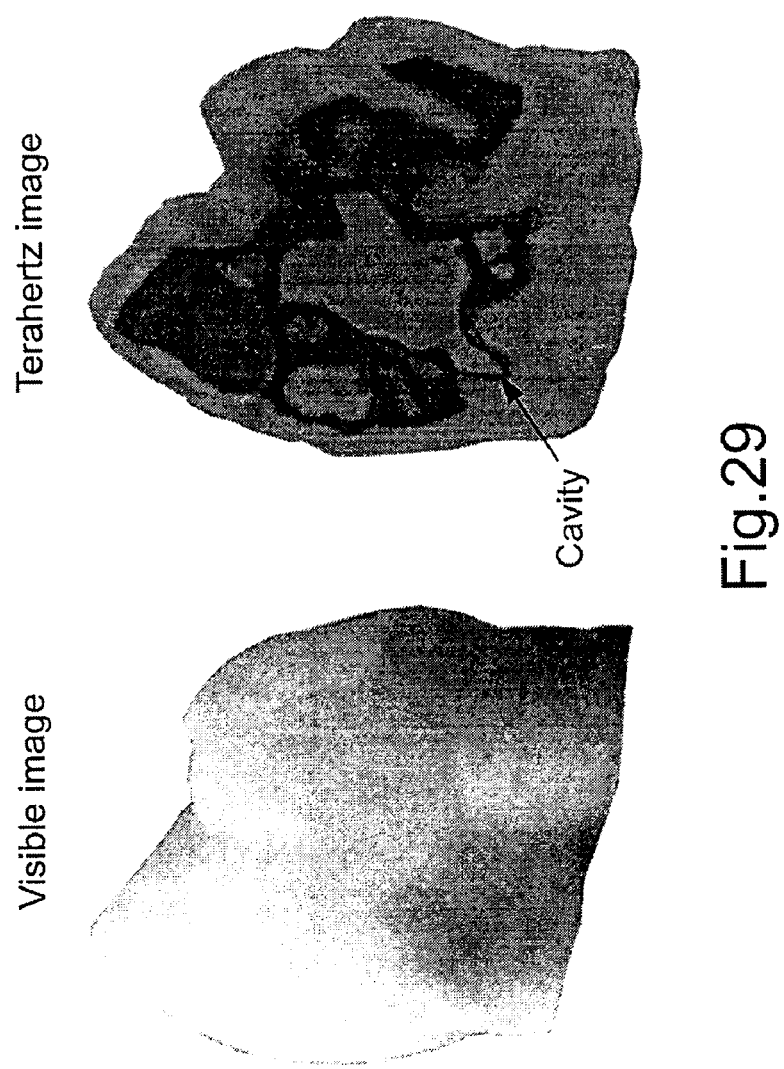

Transmission spectra of THz pulses through clotted blood
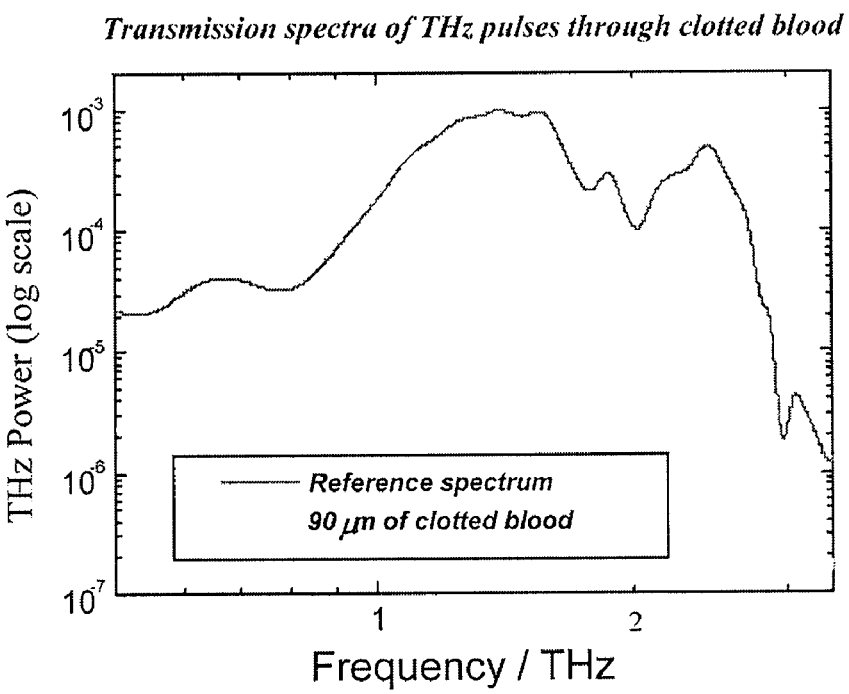
Fig.33
Example of 2 bones - visible image
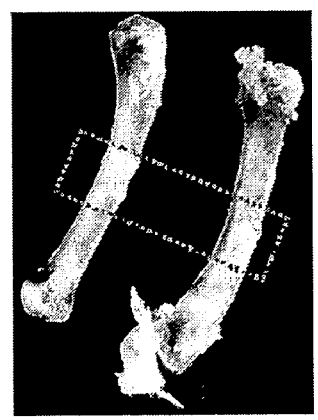
3D THz image through 2 bone sample
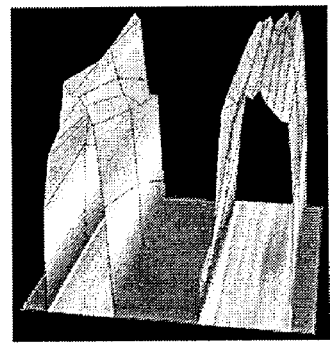
Fig.34

RADIATION PROBE AND DETECTING TOOTH DECAY

CROSS-REFERENCE TO RELATED APPLICATION

This application is a continuation of application Ser. No. 10/031,784, filed Aug. 5, 2005, which is a 35 U.S.C. §§371 national phase conversion of PCT/GB00/02849, filed 24 Jul. 2000, which claims priority of Great Britain Application No. 9917407.0, filed 23 Jul. 1999. The PCT International Application was published in the English language.

BACKGROUND OF THE INVENTION

The present invention relates to probes which can be used to image or determine compositional information from structures using radiation with a frequency from 0.1 THz to 84 THz. The present invention also relates to a method for studying diseased teeth.

Recently, there has been much interest in using THz radiation to look at a wide variety of samples using a range of methods. THz radiation can be used for both imaging samples and obtaining spectra at each pixel in an image. THz radiation penetrates most dry, non-metallic and non-polar objects like plastic, paper, textiles, cardboard, semiconductors and non-polar organic substances. Therefore, THz radiation can be used instead of x-rays to look inside boxes, cases etc. THz has lower energy non ionising photons compared to x-rays, hence, the health risk of using THz radiation are expected to be vastly reduced compared to those using conventional x-rays.

The use of THz imaging for medical purposes has been suggested. However, it is believed that the penetration depth of THz radiation might hinder imaging deep inside the human body. Also, as the human body contains a large amount of water, and water is known to be a strong absorber of THz radiation, this will also affect the useful imaging depth which can be obtained using THz radiation. Moreover, even dehydrated tissue types such a dry skin have limited penetration depths. For example, at 2.0 THz, $\alpha \sim 35$ cm$^{-1}$ for moist dermis whereas $\alpha \sim 29$ cm$^{-1}$ for dry dermis. The 1 mW average power levels that are now available suggest that only about 4 mm of moist dermis could be probed using THz.

SUMMARY OF THE INVENTION

Therefore, to address the above problems, the present invention relates to a probe assembly which has a probe which can be inserted into a human or animal body to image parts of the body or obtain spectra. Thus, the present invention could be used as a THz endoscope to probe inside the human or animal body. For example, the probe could be inserted down the throat of a patient to examine the stomach or used in key-hole surgery. Of course, the probe could be used to exam external surfaces as well.

It should be noted that although the probe will be primarily discussed for medical applications, the probe could also be used for non medical applications. For example, it could be used as a remote probe in liquid, gaseous or solid environments, or used as a safe means of delivering and detecting THz radiation to a specific part of an object under study. Remote sensing of this sort is also of particular importance in applications where imaging is required in the field or on a factory floor etc. A continuous or pulsed laser, electrical and/or optical components which may used to generate or detect the THz are often sensitive to changes in temperature, vibration etc. In these instances, the pulsed laser and/or other electronic/optical components can be placed in a controlled environment favourable to their operation that is also remote from the Terahertz measurement/imaging site.

In a first aspect, the present invention provides a probe assembly for examining a sample, the assembly comprising a probe, communicating means for communicating signals to and/or from the probe, an emitter for emitting radiation to irradiate the sample and an electro-magnetic radiation detector for detecting radiation which is transmitted or reflected from the sample, the emitter comprising a frequency conversion member which emits radiation in response to being irradiated input radiation with a different frequency to that of the emitted radiation, wherein at least one of the emitter or detector is located in the probe.

It should be noted for the avoidance of any doubt that the detector directly detects electro-magnetic radiation from the sample. It does not detect electro-magnetic radiation via a non direct method such as detecting a photo-current in the sample.

Preferably both the emitter and the detector will be located in the probe. If the emitter is located in the probe, the communicating means can be used to supply the input radiation for the frequency conversion member. It will be appreciated that only one of the emitter or detector could be located within the probe, for example the emitter could be provided within the probe and the detector could be a large fixed detector remote from the probe. Alternatively, the detector could be located within the probe and the emitter could be fixed remote from the probe.

The probe is primarily intended to be a THz probe. The emitter will emit THz radiation. However, it will be appreciated by those skilled in the art that the probe could be used with any type of radiation. In the context of this specification, THz radiation is radiation within the range of 0.1 THz to 84 THz, more preferably in the range from 0.2 THz to 20 THz. At present, there is no optical cable or the like which can transmit THz radiation without significant losses. Therefore, it is not possible to provide THz radiation directly to the probe if the emitter is located in the probe. Thus, the emitter has a frequency conversion member for converting the radiation supplied to the probe into radiation with the desired frequency range.

The probe may be configured so that the detector detects radiation which has been transmitted through the sample being examined by the probe. The probe may also be configured such that the detector detects radiation that has been reflected from the sample. The probe could also be configured to detect both reflected and transmitted radiation.

The radiation may be supplied as continuous radiation or pulsed radiation. Pulsed radiation contains a plurality of frequencies. An image can be generated from the radiation and/or compositional information may be obtained by looking at which frequency components are more strongly absorbed, or examining the modification of the refractive index or the time of flight of the pulse as it passes through the object, or a combination of these mechanisms.

Although pulsed radiation is advantageous in that it allows the sample to be imaged with a plurality of frequencies, pulsed laser diodes are more expensive and also it is difficult to send a pulse of radiation down an optical fibre. Therefore, it is also desirable to use continuous wave (CW) radiation. Such CW radiation can be supplied by CW laser diodes. In a simple configuration, CW input radiation of two different frequencies is provided as input radiation to the probe, the CW frequencies are then used to generate THz radiation using an optically non-linear member configured to generate radiation with a frequency which is substantially the difference of that of the two input frequencies. Alternatively, the two CW input frequencies could be used to generate THz radiation using a photoconductive antenna or any of the other methods referred to in this specification.

When using CW radiation to irradiate the sample, typically, the beam which has been transmitted through or reflected from the sample is compared with a reference beam to measure the change in a phase dependent quantity of the radiation as it passes through the sample. The reference beam is preferably derived from the input radiation and comprises all of the input radiation frequencies.

The above simplified case has been discussed where CW radiation with just two frequencies is used to produce THz radiation having substantially a single frequency. However, a plurality of discreet frequencies can be provided by CW input radiation to produce THz radiation having a plurality of discreet frequencies. This CW radiation may be provided by a single source running in multimode or by a plurality of single frequency CW sources. For example, three separate CW sources can be connected to the probe, each by its own fibre optic cable. If the emitter is configured to exhibit difference frequency generation, then two THz frequencies will irradiate the sample, these two frequencies can be selected to demonstrate particular contrast mechanisms in the sample which is being studied.

As has been mentioned above, it is generally necessary to provide radiation to the emitter. Preferably, this radiation will have a wavelength in the range from 600 nm to 2 µm. This radiation which will hereinafter be referred to as the 'probe radiation' is preferably provided to the probe via a fibre optic cable for example a Silicon based cable. The term probe pulse will be used to describe any radiation being supplied to the probe which is in the form of a pulse.

Although the problems of transmitting radiation of the given wavelength down a fibre optic cable are much smaller than those associated with sending THz radiation down the cable, dispersion of the radiation at optical or non-infrared wavelengths will still occur. This is not desirable as it will affect the emitted radiation.

Preferably, the probe assembly comprises a means for compensating for the dispersion of the probe radiation. This may be provided by a dispersion shifting means in the emitter which has a negative dispersion effect on the radiation. The fibre itself will have a positive dispersion effect on the radiation. Alternatively, or even in addition to dispersion shifting means, the communicating means itself (e.g. the fibre) may be provided with alternating sections which provide positive and negative dispersion effects. The negative dispersion effects could be produced using dispersion shifted fibre. This ensures that pulses of probe radiation remain compressed on arrival at the emitter.

The frequency conversion member can comprise a material which possesses good non-linear optical characteristics such that upon irradiation with radiation of a first frequency (the input radiation), it emits radiation (emitted radiation) with a frequency different to that of the first frequency. Preferably, the frequency conversion member has a crystalline structure. The following are possible materials for the frequency conversion member:

$LiIO_3$, $NH_4H_2PO_4$, ADP, $KH_2PO_4$, $KH_2ASO_4$, Quartz, $AlPO_4$, ZnO, CdS, GaP, GaAs, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, DAST (4-N-methylstilbazolium) or Si. More preferably, the frequency conversion member is configured to emit radiation with a frequency substantially equal to the difference of two frequencies of the input radiation.

It is also possible, and in some cases preferable to use other types of frequency conversion members, for example photoconductive emitters and detectors. A photoconductive emitter comprises a photoconductive member having two electrodes. To emit THz radiation, the photoconductive member is illuminated with input radiation having at least two different frequencies, upon application of a suitable bias, radiation with a frequency which is substantially the difference of the at least two input frequencies is emitted. The input radiation can be selected such that THz radiation is emitted.

The ability to supply additional power in the 25 GHz-5 THz part of the spectrum is important in endoscopic applications because most tissues have higher penetration depths (are more transmissive) at these frequencies compared to the 5 THz-20 THz band, where absorption by liquid water is more prevalent.

An advantage of these photoconductive generators and detectors is their coverage of frequencies in the range 25 GHz-500 GHz, where the peak power from the emitters is typically centred near 300 GHz-500 GHz, and extends down to 25 GHz; this can lead to large penetration depths at lower frequencies, less scattering at lower frequencies (longer wavelengths), etc. Also, phonon-related absorption/dispersion, phase matching, or other propagation effects in the emitter and detector crystals are not as problematic as they can be in some configurations using difference frequency generation (DFG) in emission and electro-optic sampling in detection. Such effects can add unwanted structure to the Terahertz time domain and frequency domain waveforms. This unwanted structure can lead to ghosts in images and can mask reflections from interfaces with small refractive index contrast—e.g. the enamel-dentine or caries-enamel interface in teeth or the stratum cornuem-epidermis or epidermis-dermis interface in skin.

Also, the amount of optical pulse energy that can be transported down a fibre is limited due to non-linear effects. Conventional fibres will typically support 20-30 mW average optical power per fibre with pulse energies in the 10 pJ-nJ range and pulsewidths in the 100 fs-1 ps, although this can vary significantly with design, material type, laser pulse repetition rate, wavelength, etc. DFG (difference frequency generation) relies on relatively high optical pulse energies (ideally at the level or larger), whereas nJ levels suffice for photoconductive generation in antenna structures with small (1-100 µm) gaps between adjacent surface electrodes, provided the average optical power is in the 10-30 mW range with pulsewidths <100 fs-1 ps and laser pulse repetition rates 10-100 MHz.

The reason for this is that in photoconductive emitters, Terahertz power is derived primarily from the acceleration of photocharge due to the applied bias on the electrodes and not the optical field out of the end of the fibre as in the case of DFG. This makes photoconductive generators particularly well-suited to low pulse energy (and hence low average power) fibre delivery systems that are used in Terahertz endoscopes.

A related advantage is that many endoscopes require compact design of not only the endoscope head, but also the near infrared/visible pulsed laser itself providing the optical radiation to the optical fibres. Amongst the most compact and rugged forms of optical pulsed lasers are Erbium doped fibre lasers or Cr:LiSapphire lasers. These lasers have reduced laser head sizes and also reduced cooling requirements (smaller power supplies and coolers are typically used relative to standard Ti:Sapphire technology, and Cr:Li Sapphire lasers can be run off batteries for limited periods). These lasers are also potentially inexpensive because of the elimination of the need for a costly pump laser. The limitation of these lasers is that many of them have average optical output powers limited to 20-50 mW. At such power levels, the optical beams used to excite the detector and emitter need to be carefully managed. A particularly efficient generation-detection scheme to use in this scenario is photoconductive generation and EOS detection. This allows the a majority of the optical power available from the optical laser to be channeled to the photoconductive switch (20-50 mW), whilst minimal power (5-20 µW) is used in the optical probe beam needed for EOS detection.

Various types of photoconductive emission devices may be used, encompassing different material systems such as low temperature GaAs, semi-insulating GaAs, silicon on sapphire, semi-insulating InGaAs, low temperature InGaAs, semi-insulating InP, low temperature InP, and As implanted GaAs. Surface electrodes based on classical dipoles embedded in transmission lines, dipoles imbedded in bow-tie antennas, and strip transmission lines may be used. Similarly, photoconductive detectors can use the above materials systems and electrode geometries. Other schemes are also known from prior art and can be incorporated.

Typically, average optical powers in excess of 20-50 mW are not useful in photoconductive emitters and detectors due to saturation and possible heating effects. Radiation or heating damage and/or limited device lifetime can result.

More preferably, the frequency conversion member is provided with phase matching means to keep the input radiation and the emitted radiation in phase with each other as they pass through the frequency conversion member. These phase matching means may be provided by varying the refractive index of the frequency conversion member, to match the phase of the emitted beam and that of a beat frequency component of the probe radiation at all points within the frequency conversion member.

In addition to the frequency conversion member, the emitter preferably further comprises a lens that focuses the probe pulse onto the frequency conversion member. The THz beam is preferably emitted through a THz collimator that forms a THz window for the probe. A filter may be provided in the emitter to prevent pulses from the probe pulse from being transmitted with the THz beam.

As has been previously described, the detector can be used to detect either transmitted THz radiation and/or reflected THz radiation. Preferably, the THz pulse emitted from or reflected by the sample is collected by a THz lens. If the detector is located within the probe, either in addition to or instead of the emitter, the detector has the same problem in that it is not viable to send the detected THz outside of the probe for analysis.

Therefore, the information carried by the emitted or reflected THz must be converted to a medium which can be transported away from the probe for analysis. Preferably, this is performed by transferring the information in the detected THz radiation to radiation of a different wavelength or by converting information carried by the detected THz radiation into an electronic form.

A preferable method for deriving information from the detected THz radiation is provided by the AC Pockels effect in what is called electro-optic sampling (EOS). Most, if not all, non-linear materials exhibit the AC Pockels effect. If a pulse of visible light is incident on a material which exhibits this effect, the visible light will be reflected and/or transmitted through the crystal without any change in its polarisation. However, if a THz pulse arrives at the same time as an optical pulse at the material, the polarisation of the optical pulse is varied via a change in birefringence induced by the THz electric field. Thus, it is possible to detect the presence of THz by passing a THz pulse and an optical pulse through a non-linear material and measuring the change in the polarisation of the optical pulse. The optical pulse is preferably the probe pulse which is also provided to the emitter. The probe assembly preferably further comprises delay means for delaying the probe pulse so that the probe pulse and THz pulse arrive at the same time at the non-linear material.

The preferred configuration for the detector works on the principle of the AC Pockels effect. Therefore, it is preferable if the detector comprises a detection member which has non-linear properties. Preferred detection members are: $LiIO_3$, $NH_4H_2PO_4$, ADP, $KH_2PO_4$, $KH_2ASO_4$, Quartz, $AlPO_4$, ZnO, CdS, GaP, GaAs, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, DAST (4-N-methylstilbazolium) or Si.

Another important application of Terahertz endoscopes is to produce spectroscopic images or diagnostic information based on high bandwidth detectors and emitters. Coverage of the far-infrared (100 GHz-20 THz) and mid infrared (20 THz-80 THz) is useful because intermolecular vibration signatures occur in the former range, whereas intramolecular vibrations occur in the latter. The ability to determine absorption and index of refraction data in these two ranges where the vibration modes are qualitatively different might enable molecules to be uniquely identified, important in the diagnosis of diseased tissue.

It is therefore important to incorporate high bandwidth capabilities into an endoscopic probe used in such applications. Detectors in such systems are ideally based on EOS due to its higher bandwidth than photoconductive detection techniques. In addition to the materials for EOS described before, gallium selenide (GaSe) may be used in EOS to allow the phase matching to be achieved at certain angles in the frequency range of interest (see for example R A Kaindl et al, Applied Physics Letters Vol. 75 no 8, 23 August 1999, pg 1060-1062). Similarly, photoconductive emitters based on p-I-n photodiodes (see for example A Leitenstorfer et al, Applied Physics Letters, Volume 74 number 11 15 Mar. 1999 pages 1516-1518) may be used in emission due to their superior performance at higher frequencies in cases where optical pump power is limited, for example 15-20 mW maximum optical pump power is typically used in such devices in free space, compared to the 100 s mW average powers typically required for DFG. In this sense, p-i-n diodes are ideal photoconductive emitters for wide bandwidth (25 GHz-80 THz) endoscopic applications.

However, a photoconductve detector could also be used, such detectors generally comprise a photoconductive material such as those previously described with reference to photoconductive emitters. Electrodes are provided on the photoconductive material, such electrodes may be surface electrodes based on classical dipoles embedded in transmission lines, dipoles embedded in bow-tie antennas and strip transmission lines may be used.

The radiation which has been combined with the THz radiation may be transmitted back to an external analysing means, it may also be separated into horizontally and vertically polarised components. These orthogonal components can then be transmitted separately (i.e. along separate optical fibres) back to an external analyser where they will be recombined into a single beam. Alternatively, the horizontally and vertically polarised components can be transmitted collinearly back to an external analyser using a polarisation preserving optical fibre.

Preferably, to save space, the optical beam is reflected in the detection member as opposed to being transmitted by the detection member. This reflected optical beam carrying the THz imaging information is then transmitted back down an optical fibre for analysis by an analysing means which is remote to the probe. The analysing means may be configured to produce an image of the sample being examined and/or to give compositional information about the sample at the point being probed.

The detector may be configured such that the probe radiation is reflected back from the detection member along a different axis to that of the incident probe radiation beam. Alternatively, the probe radiation may be supplied to the detection member and be reflected back from the detection member along the same path.

This is preferably achieved if the detector comprises a fibre optic circulator or the like. A fibre optic circulator will allow the probe radiation to be transmitted through itself to reach the detector crystal. It will then allow the reflected probe radiation to be collected by the fibre optic circulator and transmitted out of a different port to that to which the initial probe radiation was inputted into the fibre optic circulator.

The combining of the probe pulse with the detected THz radiation may also be achieved by providing a wedged surface in the detector which can be used to reflect the probe radiation to combine with the THz signal in the detection member. The detected radiation may also be further processed within detector itself. In the same manner as described above, the THz and optical pulse are combined to produce radiation which can be transmitted down a fibre optic cable. This will be referred to as visible radiation, but any radiation can be used which can be transmitted down an optical fibre can be used, which has a rotated polarisation vector due to the presence of detected THz. The visible radiation which has been combined with the THz could be passed through a variable polariser in the detector. The polariser could be set so as to block optical light which had not had its polarisation rotated by the THz.

The output from the polariser could then be read directly into a CCD array which is provided in the detector. This CCD array would then transmit information back to an image analyser. Alternatively, a plurality of optical fibres may be provided to channel the spatial variations in the probe radiation away from the detector after it has passed through the polariser. This would permit spatial variation in the THz beam to be measured via spatial variations in the probe radiation polarisation. These optical fibres could then lead to a CCD camera provided with the external analysing means. This improves spatial resolution and also affords imaging capabilities; different spatial sections of the probe radiation, encoded with different spatial areas of the THz beam, may be resolved by the CCD, leading to an image of the object from which the THz beam has been transmitted or reflected.

In use, the emitter irradiates a sample area and the detector detects radiation from this sample area. Using a CCD camera within the detector or a bundle of optical fibres within the detector to carry the signal from the polariser back to an external CCD camera allows the probe to detect spatial information from a single sample area. This technique can thus be used to improve the resolution of the probe.

The probe may comprise a single detection head which can operate as previously described. Alternatively, it may comprise a plurality of detection heads. These detection heads may be arranged in a bundle around the emitter. Each of the heads may comprise a detector as previously described to combine the THz radiation with an optical beam from the probe pulse. The optical radiation produced by this method can either be fed back to an external analysing means or the radiation from each of the detector heads can be fed to a polariser and possibly a CCD Array. A single CCD array can be provided for all of the detector heads.

Each of the fibres may be provided with its own detection member, alternatively, each of the fibres may output to a single large detection member. As the detector member and the frequency conversion member can be the same material, the detection member may also be used as the frequency conversion member. The emitter and detectors would be using different parts of the combined frequency conversion member/detection member.

Where the emitter and detector are both located in the probe, the probe can have a number of designs. It can be provided with a separate emitter and detector where the input signal to the emitter is fed through a different cable to that of the detector. The emitter and detector may be provided in the same housing, but the device may be configured so that the detector only detects transmitted radiation hence, the emitter will be on opposing side of the object to be imaged to that of the detector. The detector may also work by reflection, wherein the emitter would be spatially separated from the detector. In this case, the detector would be provided on the same side of the object as the emitter and possibly, within the same housing.

Although the detector and emitter can be housed in the same probe to perform both transmission measurements and reflection measurements, the emitter may be provided in the probe without the detector. For example, the emitter may be provided in an endoscope and the detector may be a large angle detector provided outside the body. Therefore, in a second aspect, the present invention provides a probe assembly for examining a sample, the assembly comprising a probe, communicating means for communicating signals to and/or from the probe, an emitter for emitting radiation to irradiate the sample and an electro-magnetic radiation detector for detecting radiation which is transmitted or reflected from the sample, the emitter comprising a frequency conversion member which emits radiation in response to being irradiated with input radiation which has a different frequency to that of the emitted radiation, wherein the emitter is located in the probe.

Similarly, only the detector may be provided within the probe. Therefore, in a third aspect, the present invention provide, a probe assembly for examining a sample, the assembly comprising a probe, communication means for communicating signals to and/or from the probe, an emitter for emitting radiation to irradiate the sample and an electro-magnetic radiation detector for detecting radiation which is transmitted or reflected from the sample, the emitter comprising a frequency conversion member which emits radiation in response to being irradiated with input radiation which has a different frequency to that of the emitted radiation, the detector being located in the probe and wherein information from the detected radiation is transmitted out of the probe by radiation with a different wavelength to that of the detected radiation.

The emitter is preferably of the type which requires input radiation. However, it may also be THz emitter which only requires an electrical input to generate the radiation.

The probe can be configured for many different uses. The probe can be configured as an endoscope which can be inserted into a human or animal body. The probe may also be made very small (of the order of microns) for use in key-hole surgery. Preferably, the width of the probe which is to be inserted will be less than 50 mm, more preferably less than 10 mm. More preferably, it will be less than 1 mm, or even more preferably less than 100 μm.

To produce an image, the probe assembly preferably further comprises imaging means for producing an image sample. The probe assembly may also comprise compositional and analysing means for determining information about the composition of the sample from the detected radiation. Some materials have been shown to have distinctive absorption patterns in the THz frequency regime which allows such compositional information to be determined.

The probe is particularly for use for imaging teeth. For this purpose, the probe may be provided with tooth clamping means that allow the emitter and the detector to be positioned on either side of the tooth.

THz radiation provides a valuable technique for the study of teeth and tooth disease, particularly caries. Dental caries, or teeth erosion in the enamel and dentine layers is a serious problem that affects over 90% of the UK population. With introduction of food and beverages with high sugar content and other substances, world-wide incidence of caries is expected to rise appreciably over the next decade. Frequent or regular screening of the population with a sensitive and selective imaging technique would dramatically reduce the incidence of caries, resulting in a dramatic enhancement in the dental health of the population and a large and significant cost savings to health services, insurance companies, and patients around the world.

Currently no imaging technique yields comprehensive information concerning the different types of caries at the required level of sensitivity and selectivity. Moreover, existing techniques such as x-ray radiography are not only inadequate, but raise serious safety concerns due to the use of ionising radiation in regular screening. In particular, there are serious concerns with exposing children to even semi-regular x-ray exposures.

Dental caries is commonly considered an infectious disease that causes localised destruction of the dental hard tissues by acids in the microbial deposits adhering to teeth. Caries proceeds by the creation of surface or sub-surface lesions in the enamel region. Acid, created from sugar or other substances on the tooth surfaces, permeates the enamel and forms lesions underneath or on top of the enamel surface. Eventually these lesions may grow or migrate into the dentine and begin to destroy the dentine layer. The extension of a lesion may reach the enamel-dentine junction without macroscopically visible breakdown or even microcavity formation in the enamel surface. Lesions are accompanied by demineralisation of the enamel and dentine; dentine is approximately 70% mineral, and enamel is approximately 99% mineral. Erosion is accompanied by a chemical change in the dentine or enamel, which in some cases leads to a change in water content in this region.

Previous techniques for identifying caries include visual inspection, which is not quantitative, not capable of detecting many carious lesions that are simply missed, and does not supply any appreciable diagnostic information. The other main technique is x-ray radiography. x-rays typically have a sensitivity (disease detection probability) of <=40% for primary caries, and <20% for secondary caries. Because tissue such as healthy enamel consists almost entirely of mineral, a relatively distinct loss of calcium is needed before it can be detected with x-rays.

Although, quantitative microradiography has improved considerably over the years, x-rays are considered relatively inefficient for measuring slight mineral loss in the enamel. For example, small changes in tissue porosity which accompany caries and can sometimes be detected by visible inspection often do not have enough actual mineral loss to be detected on radiograph pictures. In addition, frequent or regular screening of the population, particularly of children, would dramatically reduce the incidence of caries, but this is not possible with x-rays due to concerns over excessive and regular exposure to ionising radiation.

Near-infrared fluorescence (at $\lambda$=633 nm), polarised light microscopy, and quantitative fluorescence have also been used to detect caries, but typically are limited either by a) the ability to detect caries only after it progresses to the dentine layer and becomes infected, b) radiation scatter at these short wavelengths, c) scatter/absorption due to stains on the teeth which interrupts the signal, d) limited probe depths below the enamel surface, or e) by a combination of these mechanisms. Other imaging techniques such as ultrasound are limited by the lack of flat surfaces on teeth, or are limited by excessive cost as in the case of MRI. There is clearly a need for a more safe, selective and sensitive means of detecting caries. Moreover, none of these methods is sensitive to secondary caries. Secondary caries is the term used to describe caries which appears around tooth fillings. Moreover, secondary caries has very poor (<20%) selectivity with x-ray, and poor selectivity with optical techniques due to the presence of fillings. However, new fillings made of plastics, resins, polymers, silica, or many other materials are partially transparent at THz frequencies, allowing for easier detection of secondary caries.

Radiation in the THz frequency range is a particularly useful tool for studying teeth. Therefore, in a fourth aspect, the present invention provides a method for of detecting dental caries, the method comprising the steps of a) irradiating a tooth with a beam of radiation having at least one frequency in the range from 0.1 THz to 84 THz;

b) detecting the radiation from the tooth to obtain image data;

c) processing the image data to determine the presence of caries in the tooth.

The beam of radiation may be a pulsed beam of radiation having a plurality of frequencies or a beam of substantially continuous radiation having a single frequency or a plurality of discreet frequencies.

The method of the fourth aspect of the present invention can be used to detect primary or secondary caries.

There are many differences between a tooth with caries and a tooth without caries. The presence of caries can be detected in many ways.

In a tooth without caries, the enamel appears hard and shiny, and consists of hydroxyapatite crystals packed very tightly, such that the enamel has a glass-like appearance. The crystals in the enamel are arranged in an orderly fashion forming rods and inter-rod enamel. At the surface end (periphery) of the rods, the rod enamel is terminated in a prism shape. The packing of rods is slightly looser as regards the rod periphery compared with the rod and interrod enamel. Thus, the enamel layers are highly crystalline and possess a high degree of structural ordering. Even though the packing of crystals is very tight at the macroscopic level, each crystal is separated from its neighbours by tiny intercrystalline spaces. These spaces are filled with water and other organic materials. These spaces constitute pores in the enamel.

If mineral is removed from the enamel due to the presence of caries, the individual crystals diminish. In addition to chemical and structural changes, this demineralisation also results in an enlargement of the intercrystalline spaces that can be observed as an increase in the tissue porosity. The enamel thus becomes more porous. For this reason quantification of changes in tissue porosity can be used as an indicator of loss of mineral from the tissue.

The method of the fourth aspect of the present invention can thus be preferably configured to detect a change in the porosity of the enamel.

If the total mineral surface formed by the total mass of tightly packed crystals is considered, it is understandable that an extremely modest loss of mineral from all involved crystals results in a proportionally much more pronounced increase in the spaces between the crystals. For this reason, changes in the enamel porosity are a very sensitive indicator of even a very slight loss of mineral in the enamel. A slight increase in tissue porosity leads in turn to change in the optical properties of the enamel at visible wavelengths, which in turn leads to a change in the way in which light is scattered in the tooth. The change in the optical properties occur because the ratio of the crystalline material (e.g. hydroxyapatite, with refractive index n=1.62 in the visible) to pores (with n characteristic of the fluid in the pores, such as water n=1.33) changes, and hence the macroscopic index and other quantities such as absorption will change.

Examination of the teeth using radiation in the Terahertz frequency range i.e. 0.1 THz to 84 THz can be performed using many different techniques. THz radiation of a single frequency may be used. However, more preferably, the tooth is examined using a plurality of frequencies supplied in the form of a pulse of THz radiation.

A single frequency or a plurality of frequencies from this pulse may be detected.

Many different parameters may be measured using THz radiation to determine the presence of caries.

The absorption coefficient $\alpha(\omega)$ over the entire frequency bandwidth of the THz pulse: (a so-called panchromatic absorption image), or at a fixed frequency $\omega$ or a select, limited frequency range covered by the THz pulse (a so-called monochromatic absorption image), Thickness of the object: time-of-flight image, or Refractive index $n(\omega)$ at a fixed frequency (a so-called monochromatic image) or over the entire bandwidth: refractive index image (a co-called panchromatic image).

The applicability of these mechanisms to the detection of carious lesions in enamel are described below.

The absorption coefficient $\alpha(\omega)$ over the entire frequency bandwidth of the THz pulse, can be used to detect chemical changes associated with demineralisation. The demineralisation accompanying dental caries in the enamel leads chemical changes that can result in significant changes in the absorption band over the frequency range of 0.1 THz to 84 THz. For example, one of the major differences between regions of enamel and dentine is the extent of mineralisation; as noted above, enamel is nearly 99% mineral, whereas dentine is approximately 70%. Thus, there is heavy mineralisation in enamel relative to dentine. This results in different integrated absorption coefficients $\alpha(\omega)$ over the entire frequency bandwidth of the THz pulse the two regions.

Demineralisation will also be accompanied by differences in the water content of the two regions as well as other chemical differences such as the presence of bacteria if the regions were carious regions. Other chemical modifications that may take place in the enamel include reactions between the enamel apatite and the surrounding liquid phase. These may also have characteristic spectral signatures in the THz region, and hence form the basis of identifying caries.

In an advanced stage of caries, because of on-going acid attacks, the enamel caries lesion finally becomes so demineralised (porous) through the enamel thickness that the tissue breaks apart. A carious cavity filled with plaque microorganisms develops. This represents a significant chemical change that will produce a different absorption spectrum in the THz range what is identifiable, and diagnosable, by THz.

Changes in absorption associated with water can also be detected by THz to indicate the presence of caries.

Therefore, in a preferred method of the present invention, the image is processed to determine the water content of the tooth.

Images formed by panchromatic THz techniques are very sensitive to water content. This is demonstrated by the strong and frequency-dependent absorption spectrum associated with water. As such, the differences in water content between carious and non-carious regions (as discussed above in terms of an increase in porosity) will also allow the THz examination techniques to be used in the identification of carious regions in enamel. In particular, increased porosity near or at carious regions should lead to increased panchromatic absorption in these regions, which leads to a contrast mechanism between healthy and carious tissue using THz.

THz can also be used to look at changes in absorption associated with modification of crystallisation. Lastly, the structural differences in enamel induced by caries, namely the destruction or modification of the crystalline structure or rod/layer ordering in the enamel, will change the THz panchromatic absorption due to the modification of phonon and low frequency vibrational modes in the crystalline structure which accompanies demineralisation via caries.

Changes in absorption associated with density of material can also be detected using THz. In addition to the above parameters, then density of the material will also affect the effective absorption coefficient; the denser the material, the larger $\alpha(\omega)$ per unit volume. Thus, differences in the density of the hydroxyapatite crystals due to modification by caries, density changes induced by the material resulting from demineralisation, changes in water concentration due to porosity, etc. will all manifest themselves as changes in the $\alpha(\omega)$ and hence in the transmission through the tooth, allowing carious regions to be identified.

The above techniques are panchromatic imaging. However, monochromatic techniques where the absorption coefficient is measured over a single or limited frequency range can also be used. For the same reasons detailed above—namely differences in chemical composition due to demineralisation, variations in water content, structural differences, and density difference $-\alpha(\omega)$ at specific $\omega$ are different between healthy and carious enamel. Thus different $\alpha(\omega)$ vs. $\omega$ will permit a variety of different monochromatic transmission or absorption images at different $\omega$ to be constructed to maximise the contrast between the carious and healthy tissue.

THz can also be used to detect the thickness of the object being examined. Hence, it can be used to determine enamel thickness using a time of flight technique, i.e. measuring the time a THz pulse takes to travel through the object being examined. In certain instances, caries can reduce the thickness of the enamel. For enamel changes during tooth eruption, the final enamel surface may appear moth-eaten and in areas of the outmost microns of the enamel may disappear. These changes may not be clinically or macroscopically visible using conventional means. Other changes in enamel thickness may also accompany caries. Because THz images may be constructed from the time of flight of the THz pulse through the tooth which is directly related to the tooth thickness, TPI time-of-flight images may be used to identify carious lesions in the enamel which induce changes in enamel thickness of as little as 1 μm.

It has been previously mentioned that the refractive index can also be measured. A refractive index image is also a measure of the time of flight. The high contrast in refractive index between the enamel and the dentine+enamel results in a much longer time of flight in the enamel. Thus, by plotting the time of flight, or equivalently the refractive index $n(\omega)$, at each pixel, an image of the object may be formed.

The difference in refractive index between enamel and dentine is again likely to reflect the differences in chemical make-up, porosity, structure, and density between the two materials. Due the differences between carious and non-carious regions resulting from demineralisation and other factors, similar changes in $n(\omega)$ are likely to occur between these regions.

The refractive index can also be used to probe chemical changes associated with demineralisation. The demineralisation accompanying dental caries in the enamel should lead chemical changes that may result in significant changes in the refractive index $n(\omega)$ over bandwidth probed in THz experiments. For example, one of the major differences between regions of enamel and dentine is the extent of mineralisation; as noted above, enamel is nearly 99% mineral, whereas dentine is approximately 70%. Thus, there is heavy mineralisation in enamel relative to dentine. This results in different integrated absorption coefficients $n(\omega)$ over the entire frequency bandwidth of the THz pulse in the two regions. This difference may also reflect differences in the water content of the two regions as well as other chemical differences such as the presence of bacteria if the regions were carious regions, but the overall difference suggests that panchromatic $n(\omega)$ in the THz range is a useful mechanism for monitoring demineralisation associated with caries in enamel.

The refractive index can also be used to probe differences in the refractive index associated with water. Indeed, images formed by panchromatic THz are very sensitive to water content. This is demonstrated by the strong and frequency-dependent $n(\omega)$ spectrum associated with water, which varies from approximately 1.3 to 3.3 over the THz/infrared frequency range. As such, the differences in water content between carious and non-carious regions (as discussed above in terms of an increase in porosity) will also allow the THz panchromatic $n(\omega)$ images to be used in the identification of carious regions in enamel simply by plotting the time of flight. In particular, increased porosity near or at carious regions should lead to different $n(\omega)$ in these regions, which should lead to a contrast mechanism between healthy and carious tissue in THz.

Changes in $n(\omega)$ can also be associated with modification of crystallisation. Lastly, the structural differences in enamel induced by caries, namely the destruction or modification of the crystalline structure or rod/layer ordering in the enamel, will change the THz panchromatic $n(\omega)$ due to the modification of phonon and low frequency vibrational modes in the crystalline structure which accompanies demineralisation via caries. In addition, $n(\omega)$ is determined by the birefringence of the material, which depends on the crystalline structure in many materials. $n(\omega)$ may therefore be a tensor (not scalar) quantity in enamel, with a particular birefringence. This birefringence may change during demineralisation associated with caries, and be detected using polarisation sensitive THz.

Changes in refractive index associated with density of material. In addition to the above parameters, then density of the material will also affect the $n(\omega)$; the denser the material, the larger $n(\omega)$ per unit volume. Thus, differences in the density of the hydroxyapatite crystals due to modification by caries, density changes induced by the material resulting from demineralisation, changes in water concentration due to porosity, etc. will all manifest themselves as changes in $n(\omega)$.

As with the absorption coefficient, both panchromatic (discussed above) and monochromatic images may be formed either from time-of-flight data and/or from modelling of the complex Fourier spectrum.

When a caries lesion reaches the enamel dentine junction, the highly porous enamel lesion allows for further diffusion of acids into the dentine. An immediate reaction throughout the involved parts of the dentine is seen. Unlike enamel, dentine and the pulp cavity underneath it comprise an integral part of the living tissue with the odontoblast cytoplasmic extension running out in the thousands of tubules which form the dentine, while cell body lines the pulp chamber. Odontoblasts are similar to fibroblasts in skin and other tissue and are specialised connective tissue cells that build the dentine and subsequently maintain it.

The structural characteristics of dentine are complex. Odontoblasts lie on the inner surface of the dentine and on the periphery of the pulp. They can extend all the way from the pulp cavity up to the dentine mantle (adjacent to the enamel). They form tubules that can have lengths of up to 5 mm and typical widths of 1 μm in the dentine removed from the pulp. The spaces occupied by the odontoblastic processes as they become longer during dentogenisis (dentine growth) have the shape of long tubes extending through the mineralised dentine. They are filled with cytoplasm and gel and are called dentine tubules. The tubules are regularly arranged, the specific arrangement depending on the type of tooth and location in that tooth, and typically one might find 20,000 tubules/$mm^2$. The walls of the tubules are covered by a very dense and mineralised material referred to as peritubular dentine, which are hydroxyapatite crystals in the form of hexagonal prisms. The dental tubules with their coating of peritubular dentine are separated from each other by intertubular dentine, which is less densely mineralised. Intertubular dentine consists of collagen fibres that form an interwoven structure that lies perpendicular to the paths of the dentine tubules and enmeshes them.

When the advancing front of an enamel caries lesion approaches the enamel dentine junction, acids, enzymes, and other stimuli reach the dentine as a result of the increased permeability of the enamel. At the immediate apex of the enamel lesion, a demineralisation occurs in the dentine, which spreads peripherally through the enamel-dentine junction. This zone is called the zone of demineralisation. In the dentine tubules corresponding to the demineralisation area as well as those immediately peripheral to it, a tubular sclerosis is seen. At the centre of the lesion in the dentine, the destructive processes may be so intense that the cyotplasmic processes apparently have to retreat to the pulp cavity before they can respond.

After bacterial invasion of the enamel, the demineralised dentine layers adjacent to the enamel are also invaded by bacteria, and result in the production of a range of hydrolytic enzymes with the potential for destruction of the organic matrix of the dentine. Frequently, groups of dentinal tubules, which have been located in the centre of the demineralised dentine, appear and form a so-called dead tract that may be invaded by microorganisms. Some such tubules may also contain larger and more irregular crystals. Lastly, the reaction of the pulp to invasion of the dentine may lead to the formation of additional, irregular tubules in the dentine in much fewer numbers than the primary dentine.

Thus caries produces considerable structural and chemical modifications of the dentine.

THz can also be used to probe the area associated with the pulp cavity in a tooth. The pulp cavity consists of soft tissue including blood, water, and nerve tissue. Coupling this capability with the fact that THz can be used to probe water and blood, THz is useful for providing information on the rate of blood flow to the cavity, the presence of pulp stones in the cavity, and any bacteria or germs in the cavity region. Both panchromatic and monochromatic absorption imaging, as well as time-of-flight imaging, are useful for cavity diagnosis.

In a fifth aspect, the present invention provides a method of detecting blood flow into the pulp cavity of a tooth, the method comprising the steps of:
a) irradiating a tooth with a beam of radiation having at least one frequency in the range from 0.1 THz to 84 THz;
b) detecting the radiation from the tooth to obtain image data;
c) processing the image data to determine the flow of blood into the pulp cavity of the tooth.

The beam of radiation may be a pulsed beam of radiation having a plurality of frequencies or a beam of substantially continuous radiation having a single frequency or a plurality of discreet frequencies.

THz can also be used to detect periodontal disease. Periodontal disease affects the gums, bone and other supporting tissues of the teeth. Although most individuals suffer gum inflammation from time to time, around 10% of the population appear to suffer from the more severe forms of the disease which cause loss of supporting bone. This group appears to be at greatest risk of losing teeth through periodontal disease. The bacteria cause it that regularly collect on teeth. In particular, periodontal disease can manifest itself through a weakening of the bone below the thin skin or mucous layers at the base of the tooth. 3 major factors are thought to be responsible. Family history, stress and smoking are all-important risk factors. Stopping smoking is an important. Certain general diseases such as diabetes may also make an individual more susceptible. The signs and symptoms of periodontal disease are extremely variable but may include gums that bleed on brushing together with signs of more advanced disease such mobility or drifting of the teeth.

However, it is possible to have the disease and not aware of these signs. It is essential to attend a general dental practitioner regularly so that special assessment techniques, sometimes including X-Rays, can be carried out as part of routine dental examinations. Limitations associated with X-Rays include dangers associated with frequent screening of teeth using ionising radiation, and adequate contrast between healthy and weakened bone. Periodontal disease is also traditionally diagnosed by measuring the depth of the sulcus, or cuff, about the teeth, as well as by using dental radiographs that demonstrate the height of alveolar bone. These diagnostic procedures have changed little in the past 40 years. Now, however, there is considerable interest in the development and application of new diagnostic test that allow periodontal disease to be diagnosed and the effects of treatment monitored on a regular basis.

In a sixth aspect, the present invention provides a method of detecting periodontal disease in a tooth, the method comprising the steps of:
a) irradiating the bone supporting a tooth with a beam of radiation having at least one frequency in the range from 0.1 THz to 84 THz;
b) detecting the radiation from the bone to obtain image data;
c) processing the image data to determine the presence of periodontal disease.

The beam of radiation may be a pulsed beam of radiation having a plurality of frequencies or a beam of substantially continuous radiation having a single frequency or a plurality of discreet frequencies.

THz can be used to image bone. Moreover, changes in the 1) density, 2) hardness, 3) structure, or 4) chemical composition will result in changes in the quantities responsible for contrast mechanisms available by using THz.

The methods of the fifth and sixth aspects of the present invention can benefit if the data is processed to determine the absorption coefficient of the tooth or bone or the refractive index of the tooth or bone.

The image derived in the method of any of the second to fourth aspects of the invention can be processed to determine differences in the composition of the tooth or, it can be used to determine the exact composition of the tooth or bone. A particularly preferable method of producing the image can be achieved by comparing radiation from the tooth or bone which is not passed through the tooth or bone, calculating the delay between radiation which is passed through the tooth or bone and radiation which has not passed through the tooth or bone and plotting the delay for different points of the tooth or bone.

The data derived from the detected THz can be used to determine compositional information of the tooth or bone. It can also be used to detect the presence of bacteria which have been found to affect the absorption characteristics of the tooth.

In a seventh aspect, the present invention provides an apparatus for imaging caries in teeth, the apparatus comprising:
a) means for irradiating a tooth with a beam of radiation having at least one frequency in the range from 0.1 THz to 84 THz;
b) means for detecting the radiation from the tooth to obtain image data;
c) means for processing the image data to determine the presence of caries in the tooth.

The beam of radiation may be a pulsed beam of radiation having a plurality of frequencies or a beam of substantially continuous radiation having a single frequency or a plurality of discreet frequencies.

In an eight aspect, the present invention provides an apparatus for imaging periodontal disease in teeth, the apparatus comprising means for irradiating the bone located below a tooth with a beam of radiation having at least one frequency in the range from 0.1 THz to 84 THz;
means for detecting the radiation from the bone to obtain image data;
means for processing the image data to determine the presence of periodontal disease.

The beam of radiation may be a pulsed beam of radiation having a plurality of frequencies or a beam of substantially continuous radiation having a single frequency or a plurality of discreet frequencies.

In a ninth aspect, the present invention provides an apparatus for imaging the blood flow into the pulp cavity of a tooth, the apparatus comprising:
a) means for irradiating a tooth with a beam of radiation having at least one frequency in the range from 0.1 THz to 84 THz;
b) means for detecting the radiation from the tooth to obtain image data;
c) means for processing the image to determine the presence of blood flow into the cavity.

The beam of radiation may be a pulsed beam of radiation having a plurality of frequencies or a beam of substantially continuous radiation having a single frequency or a plurality of discreet frequencies.

Preferably, the imaging means according to any of the seventh to ninth or seventh aspects of the present invention comprises means for comparing the radiation from the tooth or bone with radiation which has not passed through the tooth or bone, means for calculating the delay between radiation which has passed through the tooth or bone and radiation which has not passed through the tooth or bone, and means for plotting the delay for different points of the tooth or bone.

Preferably, the means for irradiating the tooth and the means for detecting radiation from the tooth or bone are located in a probe which can be placed in a human or animal mouth.

The present invention will now be further described with reference to the preferred non-limiting embodiments in which:

BRIEF DESCRIPTION OF THE DRAWINGS

FIGS. 7A and 7B show variations on the detectors of FIGS. 5 and 6;

FIG. 8 shows a variation on the detectors of FIGS. 5 to 7;

FIG. 9 shows a variation on the detector of FIG. 8;

FIGS. 23A and 23B show photographs of a human tooth, FIG. 23C shows a CCD image of the tooth of FIGS. 23A and 23B;

FIG. 24A shows the CCD scan of FIG. 23C,

FIGS. 24B to 24D show time domain THz pulses as they pass through the three regions denoted with reference to FIG. 23 and FIG. 24E shows a plot of the temporal shift of the measured peaks from FIGS. 24B to 24D against x-axis, FIGS. 24E and 24F illustrate how the THz changes throughout the oath of the tooth;

FIG. 28 shows a two dimensional contour plot of the tooth of FIG. 16;

FIG. 29 shows a panchromatic absorption image of the tooth of FIG. 16;

FIG. 33 shows a plot of THz transmission against frequency through clotted blood; and FIG. 34 shows a bone image taken using THz transmission.

DESCRIPTION OF PREFERRED EMBODIMENTS

Figure 1:
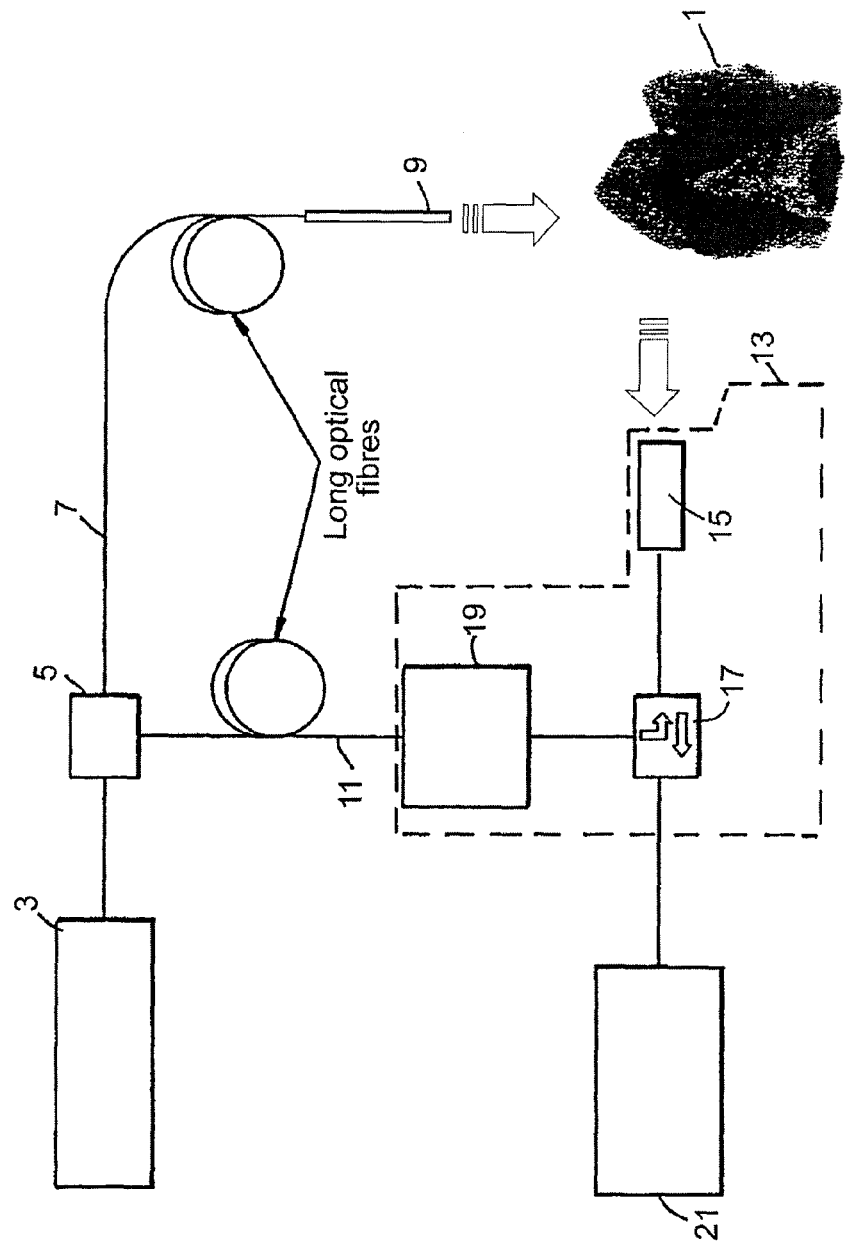
FIG. 1 shows a schematic outline of a THz probe according to an embodiment of the invention.

FIG. 1 shows a schematic outline of the functions of the THz probe. The object to be examined by the probe is tooth 1. An ultra fast laser source 3 provides pulsed radiation to a beam splitter 5. (Although, a continuous wave source could also be used as will be explained in relation to FIGS. 17 to 19). Beam splitter 5 then splits the beam to travel along two fibre optic cables 7, 11. Fibre optic cable 7 is connected to the THz emitter 9. Fibre Optic 11 is provided to the THz detection system 13. The THz detection system 13 has a THz detector 15 which detects radiation which is either passed through and/or been reflected from the tooth 1. The delay control may alternatively be placed in the fibre optic cable 7 leading to the THz emitter 9.

Information from the detected THz beam is then encoded onto the laser source beam from fibre optic cable 11. Fibre optic circulator 17 is in effect a radiation valve which is used to direct the beam from fibre 11 into the THz detector for encoding with the information from the detected THz, and it is used to direct the beam with the encoded THz information into polarisation bridge 21. Before the THz beam and the reference beam are combined (such that the reference beam can carry information from the detected THz), the reference beam is passed through delay control means 19 to match the temporal shift of the reference beam with that of the detected THz signal. The encoded THz information is then derived using polarisation bridge 21. Details of the polarisation detection system will be described with reference to FIG. 10

Figure 2:
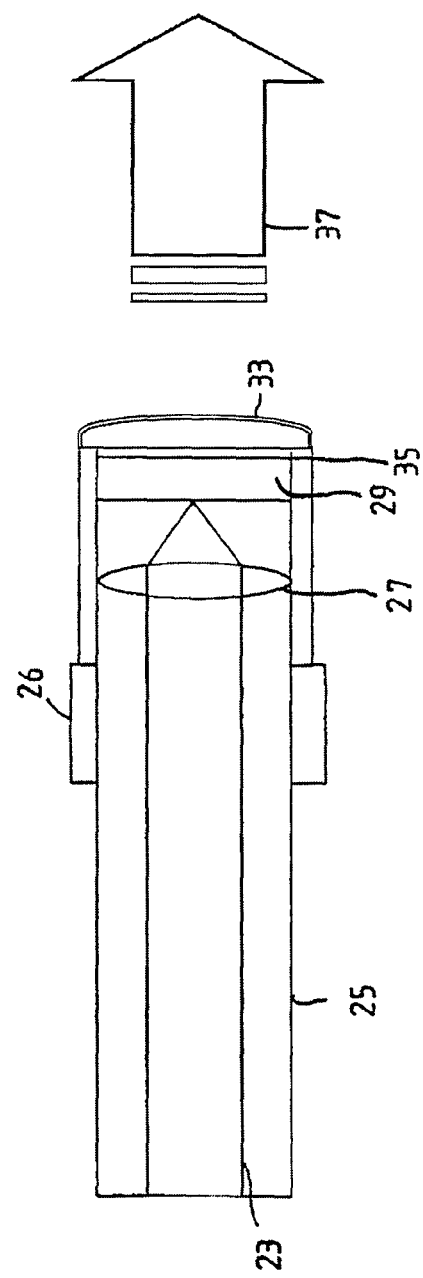
FIG. 2 shows an emitter for use with the THz probe in accordance with a preferred embodiment of the first aspect of the present invention.

FIG. 2 shows a further configuration for the emitter. A beam 23 (pump pulse) taken from optical fibre 7 (FIG. 1) is directed into probe housing 25. A focusing lens 27 is provided in the probe housing 25. The focusing lens 27 focuses the beam 23 onto a non-linear crystal 29. The non-linear crystal which is the THz emitter is configured to emit radiation with at least one frequency in the range from 0.1 THz to 84 THz (colloquially known as "THz radiation") when it is irradiated with beam 23. In this particular example, the non-linear crystal is configured to emit radiation with a frequency which is substantially equal to that of the difference of two frequencies of the incident radiation.

Part of the housing 25 is covered with a protective sleeve 31. The housing 25 has a fibre coupler 26 for connecting fibre optic 7 to the housing. At the end of the housing there is a protective cover 33. Behind this protective cover is a filter for residual visible pulses 35. The protective cover may also function to be a collimator for the THz beam. The THz beam 37 is thus emitted through the protective cover 33. The collimator may be an Si polyethylene lens, or a lens made out of other suitable (non-absorbing and non dispersive THz) material. The collimator might also be configured to focus the THz to a spot on the sample, or be configured to supply a given THz beam profile which matches the THz beam to the detector after reflection or transmission from the object 1 under study. In addition to a lens, a condensing cone may also be provided.

Figure 3:
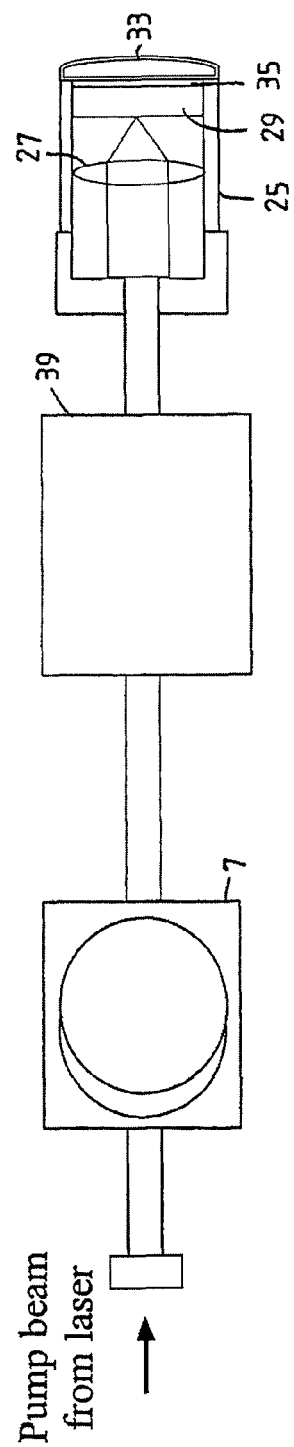
FIG. 3 shows a variation on the emitter of FIG. 2.

FIG. 3 shows a further example of an emitter. The emitter housing 25 is the same as that shown in FIG. 2. The details of the component within the housing 25 will not be repeated. Like reference numerals denote like features between FIGS. 2 and 3. The beam 23 is supplied to the emitter housing 25 from fibre optic cable 7. Ideally, this fibre optic cable is a minimum dispersion fibre which has a positive dispersion effect on pulses travelling through the fibre. There is a problem that over long length optical fibres, the radiation being carried by the fibre disperses which causes inaccuracies and unwanted modifications in the THz generation because the pulses initially provided by the laser beam have become lengthened in time. In order to compensate for this problem, the pulses are passed through a dispersion compensator 39 which compresses the pulses in time prior to focusing on the generation crystal 29. The dispersion compensator 39 has a negative dispersion effect on the pulses whereas the minimum dispersion fibre has a positive dispersion effect on the pulses.

Figure 4:
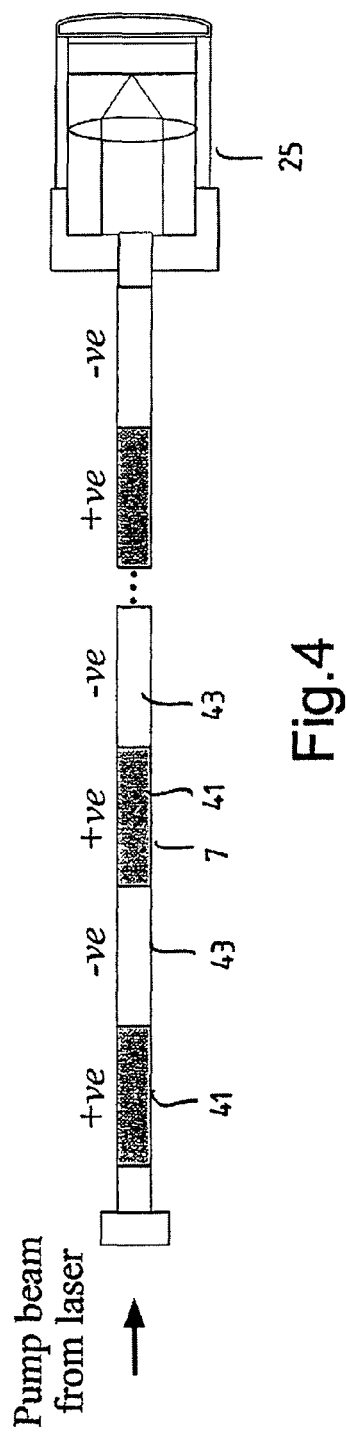
FIG. 4 shows a variation on the emitters of FIGS. 2 and 3.

FIG. 4 shows a further configuration of optical fibre 7 for compensating for the dispersion effects which occur in the optical pulse when it is passing through the fibre 7. Here, the optical fibre 7 is provided with positive dispersion segments 41 which serve to increase dispersion of the pulse and negative dispersion segments 43. The negative dispersion segments cancel out the effect of the positive dispersion segments. Therefore, the pulses remain compressed on arrival at the emitter housing 25.

Figure 5:
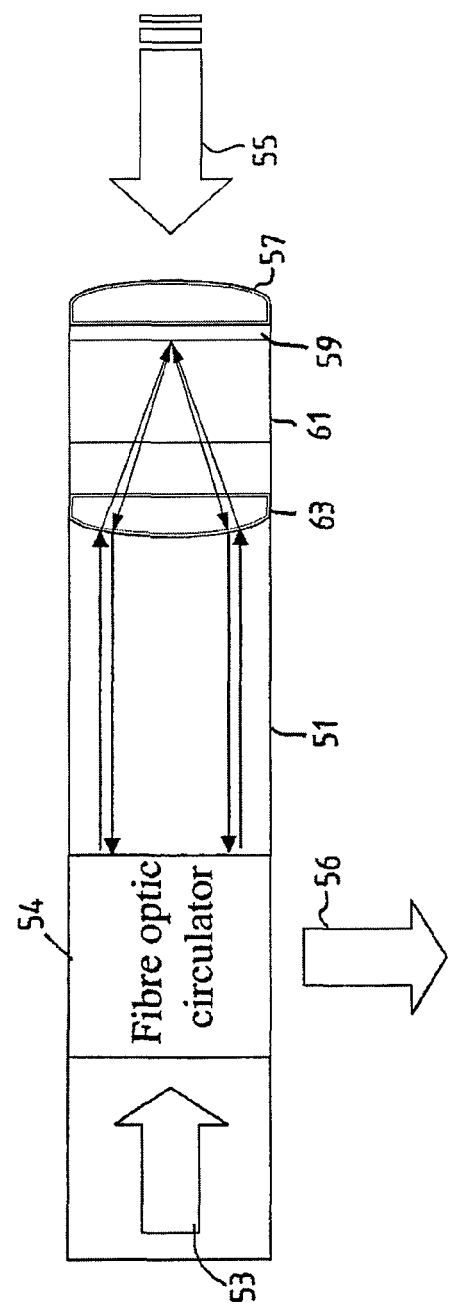
FIG. 5 shows a detector in accordance with a preferred embodiment of a first aspect of the present invention.

FIG. 5 shows an example of a detector. The detector is provided in housing 51. The detector is provided with a reference beam (or probe pulse) 53 which is taken from fibre optic cable 11 (FIG. 1). The probe pulse 53 is passed through fibre optic circulator 54 from a first port of the circulator and out through a second port of the circulator, onto lens 63 which serves to focuses the probe pulse 53 onto a detection member 61.

The detection member 61 is a non-linear crystal which, will transmit the probe pulse. However, if the probe pulse 53 mixes with a THz pulse 55 in the detection member 61, the polarisation of the probe pulse will be rotated due to the birefringence caused by the THz pulse. This effect is known as the AC Pockels effect and the detection technique is generally called electro-optic sampling (EOS). The change in polarisation of the probe pulse can be detected by known techniques.

The probe pulse 53 is reflected back through detection member 61 by mirror 59 which is located on the opposite side of the detection member 61 to the point of entry of the probe pulse 53 into the probe.

A THz pulse 55 which is either transmitted by or reflected from the sample is collected by THz lens 57. The lens 57 may alternatively be a condenser cone, or a combination of a lens and a condenser cone. The pulse 55 then passes through dielectric layer 59 which is provided behind the THz lens 57. The dielectric layer 59 enhances the reflection efficiency of the probe pulse. The dielectric layer is highly transparent at THz frequencies, thus it transmits the THz. The THz pulse then passes through detection member 61 and combines with the probe pulse 53 to rotate the polarisation of the probe pulse.

The reflected probe pulse then passed back onto the fibre optic circulator 54 through the second port of the circulator. The fibre optic circulator transmits the reflected probe pulse out of a third port of the circulator. The transmitted probe pulse 56 which carries the information from the detected THz pulse 55 is then carried by a fibre optic cable to an external analysing means.

Figure 6:
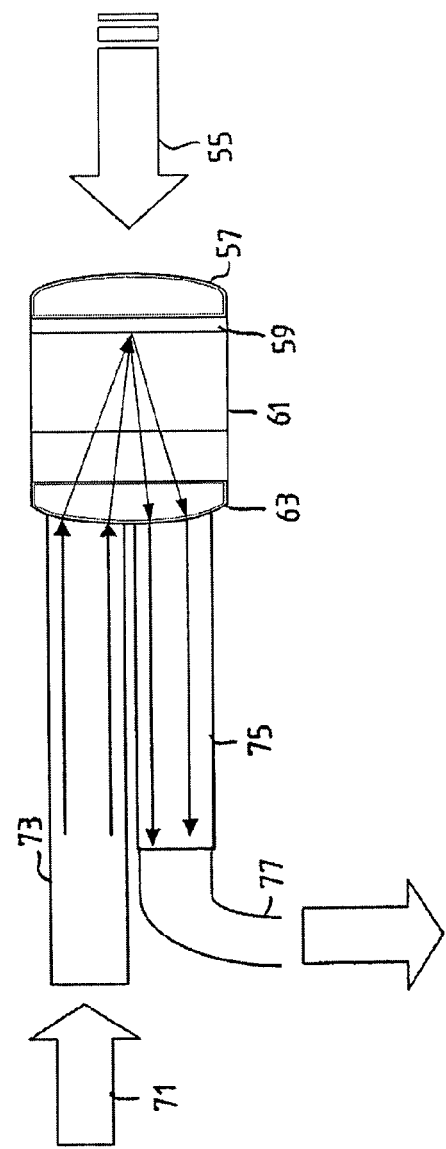
FIG. 6 shows a variation on the detector of FIG. 5.

FIG. 6 shows another variation on the detector. Here, separate fibres are used to deliver and collect the probe pulse to and from the detection member 61 respectively. The probe pulse 71 is essentially the reference beam. To avoid repetition, the features which are the same as those shown in FIG. 5 will be given the same reference numerals and will not be described here. As for FIG. 5, the THz beam is transmitted into electro-optical medium 61. The probe pulse which will be at optical frequencies is transmitted down channel 73 through focusing lens 63 into electro-optical medium which it combines with the THz pulse 55. The THz pulse affects the polarisation characteristic of the probe pulse 71. Therefore, the polarisation of the probe pulse can be used to determine the presence of the THz beam. The probe pulse 71 is then reflected into channel 75 and then into optical fibre 77 for analysis.

Figure 7A:
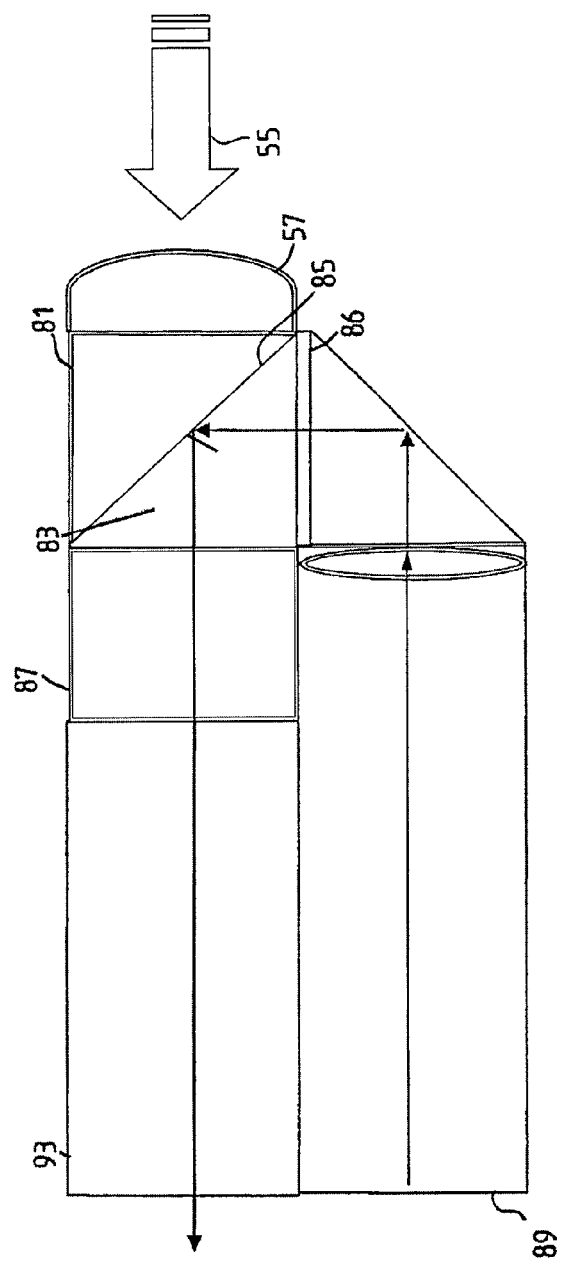

FIGS. 7A and 7B show further examples of the detector. Here, the THz pulse is collected by THz lens 57. The THz pulse 55 passes through the lens 57 and is directed onto material A 81 which is transparent to THz. The THz pulse is transmitted through material A and through material B 83 which is adjacent to material A. Material B is transparent to both THz and visible light. A reflective coating 85 is provided on the junction between materials 81 and 83. The reflective coating 85 is transparent and non dispersive to THz radiation. The boundary between materials 81 and 83 is inclined at an angle of about 45° to that of the incident THz pulse, and hence the reflective coating is inclined at an angle of about 45° to that of the incident THz pulse. An anti-reflective coating 86 is provided where the probe pulse enters Material B 83, to avoid unwanted reflections.

Adjacent material B is an electro-optical medium 87. Here, the THz pulse and the visible pulse will be combined. The incident probe pulse enters through channel 89. The incident probe pulse is then focused by lens 91. This lens functions to focus the incident probe pulse at the electro-optical medium 87. A wedge is provided to reflect the incident probe pulse into material B and hence onto the electro-optical medium 87 via the interface between materials A and B. Material A is not transparent to the optical pulse. The optical signal with the THz data is then transmitted away from the probe via channel 93.

Alternatively, Material B 83 may be electro-optic material (which can serve as the detection member), and the modification of the probe pulse polarisation due to the presence of THz may occur in Material B 83 in addition to or instead of medium 87.

In FIG. 7B, a liquid crystal variable waveplate 88 is provided such that the probe pulse with the encoded THz information passes through this after passing through material 87. This plate can be used to block radiation with a certain polarisation, or it can be used to rotate the polarisation of incident radiation.

FIG. 8 shows yet another variation on the detector arrangement of FIG. 7. To avoid unnecessary repetition, the same reference numerals in FIG. 7 are used in FIG. 8 and the description thereof will not be repeated. Here, lens 91 functions not to focus the optical pulse of the electro-optical medium 87 surface. Instead, it expands the incident probe pulse to fit the whole of the electro-optical medium 87 surface.

The incident probe pulse is inserted into the detector via channel 89 (as described with reference to FIGS. 7A and 7B). The pulse is then reflected in the same manner into the electro-optical medium 87 where it is combined with the THz pulse 55. A probe pulse carrying the THz information is then passed through liquid crystal variable retarder 95. The retarder can block optical pulses with a specific polarisation, it can also be used to rotate the polarisation of pulses if required. As previously explained, the THz beam serves to rotate the polarisation of the probe pulse. Therefore, by setting the retarder to block polarisation at the original polarisation of the incident probe pulse, the retarder will block any optical pulses with a polarisation which has not been rotated by the THz.

FIG. 9 shows a variation on the detector of FIG. 8. Again, like components will have the same reference numerals. The only difference between these two is instead of the CCD array 97 provided within the detector itself, an optical fibre bundle 99 collects the output from the liquid crystal retarder 95. Each fibre of the optical fibre bundle 99 can be thought of as representing a pixel. The optical fibres will be polarisation preserving fibres which do not destroy the polarisation of the probe pulse as it travels towards an external analyser. Each fibre of the bundle 99 will carry spatial information back away from the probe. This improves spatial resolution and/or provides enhanced imaging capability.

Figure 10:
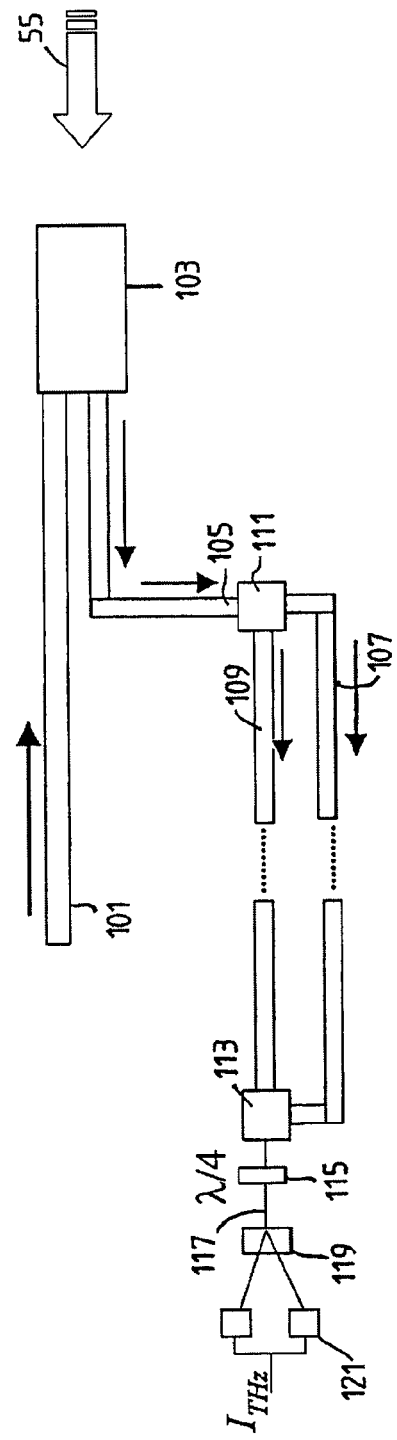
FIG. 10 shows a variation on the detector principle.

FIG. 10 shows a detection system which can be used with any of the detectors of FIGS. 5 to 9. The incident probe pulse is supplied via channel 101 to the detection head 103. The THz pulse 55 is collected by detection head 103. The THz pulse 55 and the visible probe beam 101 are combined in the detection head. The retarded visible probe is channeled away from the detection head via channel 105. Here, the pulse is split into horizontally 107 and vertically 109 polarisation's via beam splitter 111. The horizontal and vertical polarised beams are then transmitted down separate fibre optic cables to a balanced detection system 113 located in the control apparatus for the detector.

The applicant wishes to clarify that the angle Θ through which the polarisation is rotated by is negligible when there is no THz present, the linearly polarised beam can become slightly elliptical. This effect is compensated for by a variable retardation waveplate, e.g. a quarter waveplate 115.

The beam from the detector 105 is converted into a circularly polarised beam 117 using quarter wave plate 115. This is then split into two linearly polarised beams by a Wollaston Prism 119 (or equivalent device for separating orthogonal polarisation components) which directs the two orthogonal components of the polarised beam onto a balanced photo-diode 121. The balanced photodiode signal is adjusted using wave plate 115 such that the difference in outputs between the two diodes is zero when no THz is detected.

However, if the detector detects a THz beam, the angle Θ through which the polarisation is rotated by is not negligible. This is because the THz electric field modifies the refractive index of the visible (fundamental) radiation along one of the axes $n_e$, $n_o$. This results in the visible field after the detector being elliptical and hence the polarisation components separated by the prism 119 are not equal. The difference in the voltage between the output diodes gives a detection voltage.

The probe pulse 101 and the THz beam 55 should stay in phase as they pass through the crystal detection member. Otherwise the polarisation rotation Θ is obscured. Therefore, the detection member has phase matching means to produce a clear signal.

Figure 11:
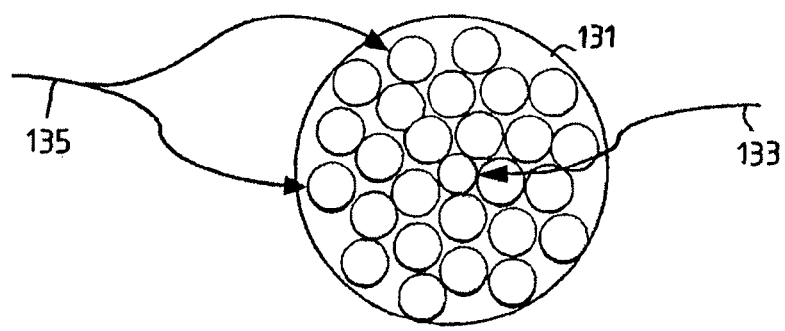
FIG. 11 shows a probe in accordance with the first aspect of the present invention with a plurality of detector heads.

FIG. 11 shows a multiple detector design. The emitter and detector are housed in housing 131. An emitter 133 is provided in the centre of the housing 131. Multiple detector heads (fibre optical cables) 135 are provided around the emitter 133. The detector head 135 can be any of those described with reference to FIGS. 5 to 9. Also, the emitter can be any of those described with reference to FIGS. 2 to 4. The number of detectors will vary depending on the application and spatial resolution required. Alternative designs may be used with only a bundle of detectors and with an emitter as a single fibre source, which is spatially separated from the detector heads 135.

Figure 12:
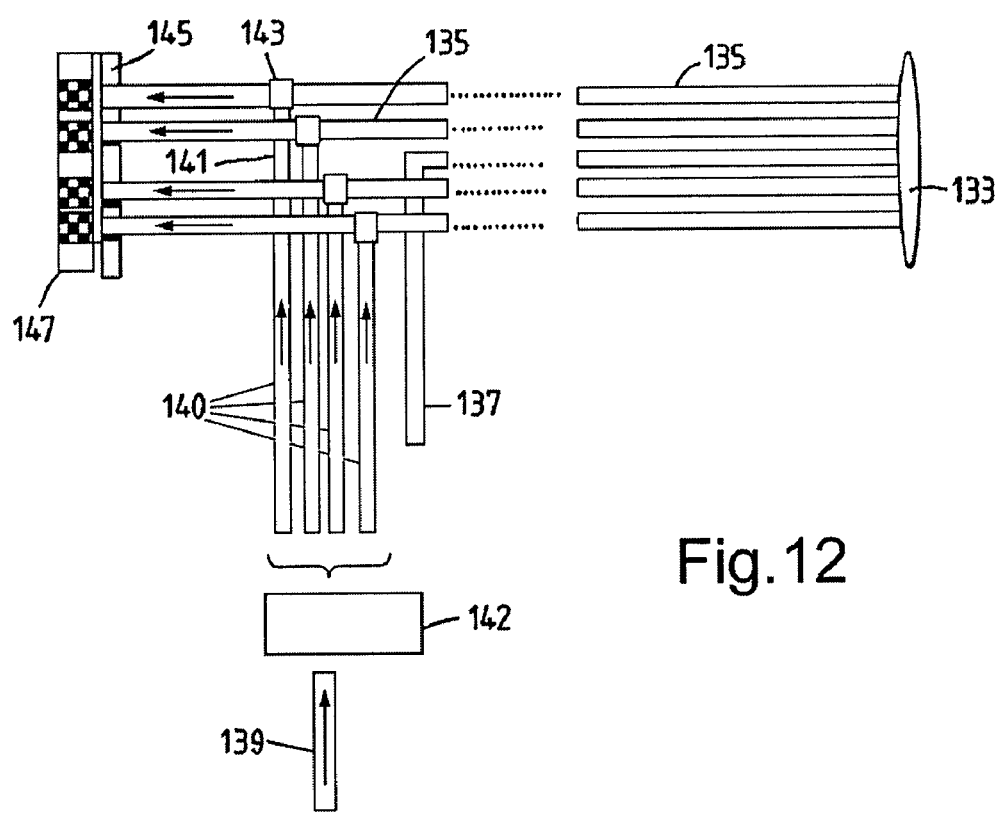
FIG. 12 shows the detector of FIG. 11 in more detail.

FIG. 12 shows a further variation on the multiple detector design. A plurality of detector heads 135 are arranged around emitter 133. The emitter is provided with a generation pulse from channel 137. The detected THz radiation is picked up by fibres 135. The probe beam for each fibre is provided by bundle of fibres 140, which itself is provided from single optical fibre 139 via a coupling means 142. A probe signal from each single fibre 141 of bundle 139 is directed into the detector head via fibres 135, and modified probe beam in 135 which contains the encoded THz signal is coupled via 143 into the polariser array 145 and then CCD array 147. The polariser array 145 is crossed relative to the polarisation of the incident probe beam from fibre 139. The multiple detector heads can be configured to have separate electro-optical crystals for each fibre or alternatively, a single electro-optic crystal for use with all fibres. The this case, both the detector and the emitter could use the same electro-optic member.

Other types of emitter may be used which also emit radiation with a frequency in the desired range in response to irradiation by one or more input beams which can be carried to the probe by one or more optic fibre cables.

Figure 13:
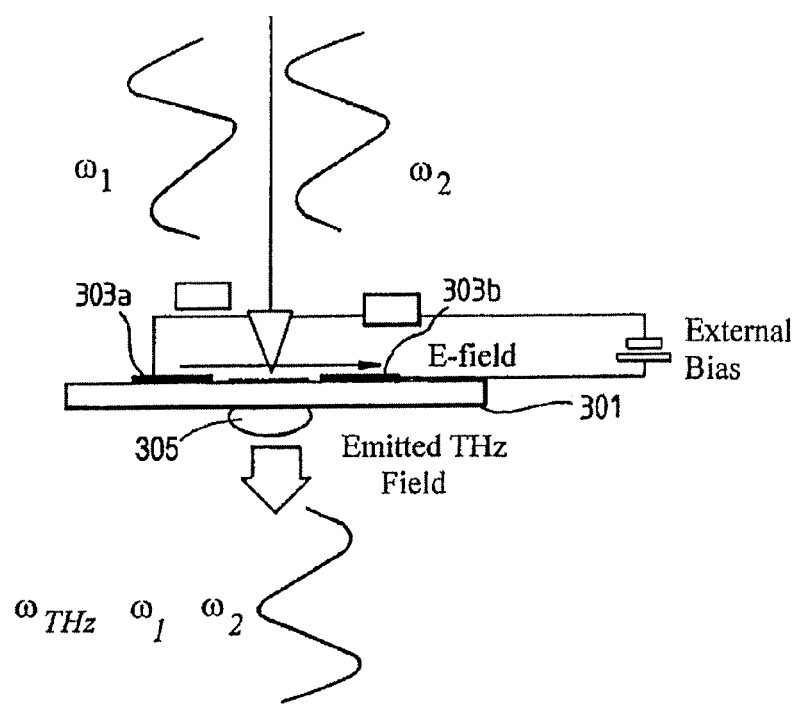
FIG. 13 shows a photo-conductive emitter which can be used as the frequency conversion member in accordance with an embodiment of the present invention.

FIG. 13 illustrates a so-called photoconductive emitter. The emitter comprises a member 301 comprising a semiconductor such as low temperature GaAs, semi-insulating GaAs, silicon on Sapphire, semi-insulating InGaAs, low temperature InGaAs, semi-insulating InP or As implanted GaAs, etc. The semiconductor member has a pair of electrodes 303a and 303b located on its surface, the electrodes 303a and 303b are connected to a power supply such that a field can be generated between the two electrodes 303a and 303b.

The simplest electrode arrangement is shown in FIG. 13. However, the electrodes may be triangular and arranged in a bow-tie shape, a so-called bow-tie antenna or they may be interdigitated electrodes at the centre of a bow tie or spiral antenna. Alternatively, such designs may be incorporated into transmission lines on the chip.

The semiconductor member is irradiated by two pump beams with frequencies ω1 and ω2. The pump beams impinge on the semiconductor member 301 on the part of its surface between the electrodes 303a and 303b, i.e. where the field is applied. The beating of the two visible or near-infrared lasers in the non-linear region of the semiconductor member between the two electrodes 303a and 303b results in the emission of THz radiation from the semiconductor member 301. The semiconductor member 301 is provided with a lens 305, which may be of a hemispherical or other design, on its surface which is opposite to that of the surface with the electrodes, to allow the emission of a beam of THz radiation.

The emitter of FIG. 13 can also be configured as a photoconductive detector. THz radiation is incident on a back surface of the semiconductor member 301. On the opposing side of the semiconductor member 301 are located a pair of electrodes 303a and 303b. The region between these two electrodes 303a and 303b is illuminated by radiation of the visible or near infrared range (probe pulse). As the detector needs to know information about the phase of the radiation emitted from the emitter 1 this radiation preferably carries such information. Typically, the THz radiation which is used to image the sample will be derived from this radiation. The near-infrared/visible radiation illuminates the surface of the detector between the electrodes 303a and 303b. The Terahertz radiation induces a photocurrent through the region between the electrodes 303a and 303b which is being illuminated by the visible/infrared radiation. The current which can be detected by the electrodes is proportional to the strength of the THz field.

The electrodes 303a and 303b may be of a simple diode formation embedded in a transmission line. Alternatively, they may be triangular and arranged in the shape of a bow-tie to from a so-called bow-tie antenna. They may also be inter-digitated electrodes at the centre of a bow-tie or spiral antenna.

Figure 14:
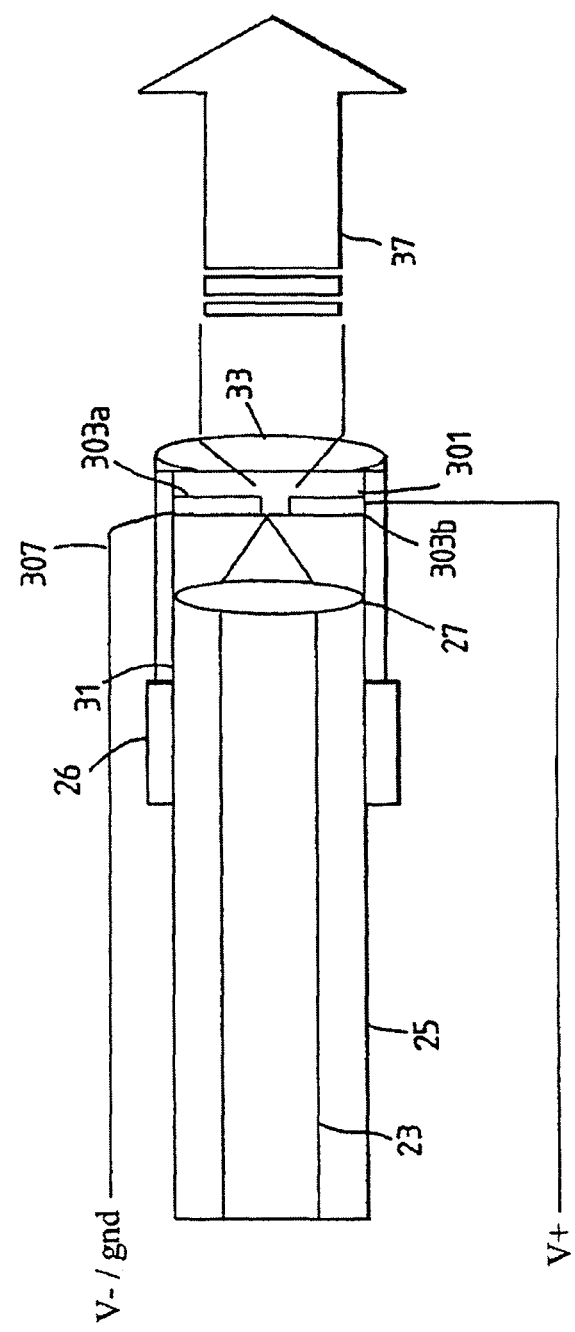
FIG. 14 shows a probe in accordance with a preferred embodiment of the present invention having a photo-conductive emitter.

FIG. 14 shows the photo conductive emitter of FIG. 13 in a probe in accordance with an embodiment of the present invention. It will be noted that the arrangement is very similar to that of FIG. 2. Therefore, to avoid unnecessary repetition or confusion, like reference numerals will be used to denote like features.

As shown in FIG. 2, a pump beam 23 is taken from optical fibre 7 (FIG. 1) and is directed into probe housing 25. A focusing lens 27 is provided in the probe housing 25. The focusing lens 27 focuses the beam 23 onto photo conductive emitter body 301. The photo conductive emitter body is the same as that described with reference to FIG. 13. Electrodes 303a and 303b overlying said emitter body are biased to create a field between themselves. In this specific example, electrode 303a is connected to ground via wire 307 and electrode 303b is connected to a positive bias via wire 309. THz radiation is generated as explained with reference to FIG. 13.

As described with reference to FIG. 2, the part of the housing is covered with the protective sleeve 31. The housing 25 has a fibre coupler 26 for connecting fibre optic 7 to housing 25. At the end of the housing, there is a protective cover 33. Behind this protective cover is a fibre for residual visible pulse 35. The protective cover may also function as a collimator for the THz beam. The THz beam 37 is thus emitted through protective cover 33. As previously described, the collimator may be a Si polyethylene lens, or a lens made out of other suitable (non-absorbing and non-dispersive THz) material. The collimator might also be configured to focus the THz beam to a spot on the sample, or be configured to supply a given THz beam profile which matches the THz beam to the detector after reflection or transmission from the object 1 under study. In addition to a lens, a condensing cone may also be provided.

Figure 15:
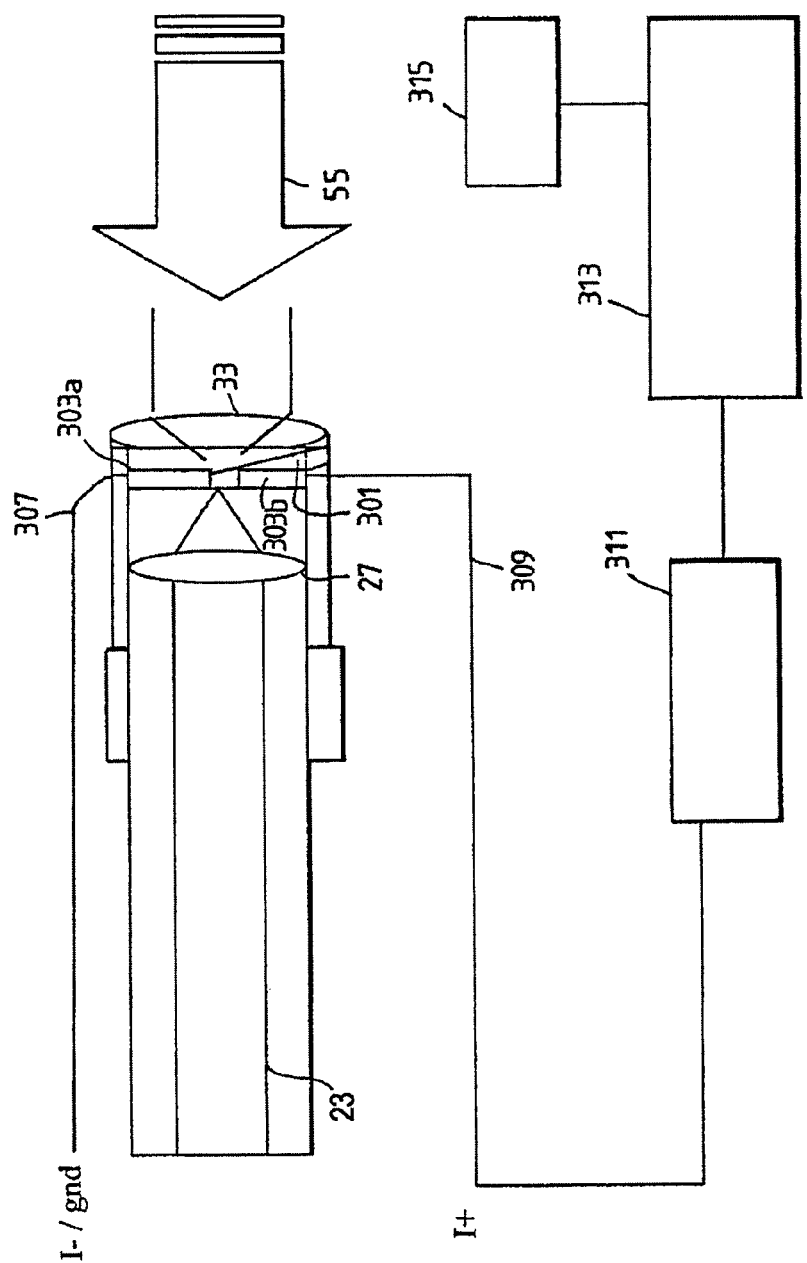
FIG. 15 shows a probe in accordance with a preferred embodiment of the present invention having a photo-conductive detector.

FIG. 15 shows a detector housed in a probe using a photo conductive detector. It should be noted that the design is very similar to that described with reference to FIG. 14. In this situation, pump pulse 23 is provided to the probe from optical fibre 7. The pump pulse is focused via lens 27 onto photo conductive antenna body 301 as described with reference to FIG. 14.

The pump pulse photo excites electron hole pairs. In this example, no bias is applied across electrodes 303a and 303b. Therefore, there is no incentive for the photo excited carriers to move towards either electron 303a or 303b. However, such an incentive is provided by THz beam 55. The THz beam enters the detector through protective cover 33. It then impinges on photo conductive antenna body 301 and causes the photo excited carriers to move either towards electrode 303a or 303b resulting in a current slowing from lead wires 307 to 309. In this example, the current is carried away by wire 309. The change in the phase of the THz radiation as it passed through the sample can be detected by measuring the induced current. The current is then amplified using pre-amp 311. The pre-amp output is then fed into locking amplifier and/or AD converter and/or signal processor 313 which is then analysed by computer 315.

As described with reference to FIG. 11, a plurality of detectors as described with reference to FIG. 15 can be the detector heads 135 as described with reference to FIG. 11. An emitter as described with reference to FIG. 14 or for example, any other type of emitter described previously can be seen as emitter probe 133. Of course, it will be appreciated that other types of detector is described with reference to the preceding figures could be used as detector heads 135 in combination with a photo conductive emitter 133.

It can be seen from the similarity between FIGS. 14 and 15 that essentially the same arrangement can be used for either the detector or the emitter. However, the bias conditions on the electrodes 303a and 303b will be different dependent on whether or not the probe is to work as an emitter or detector. As a result, a detector head or emitter head can be easily interchanged by applying the appropriate biases.

Figure 16:
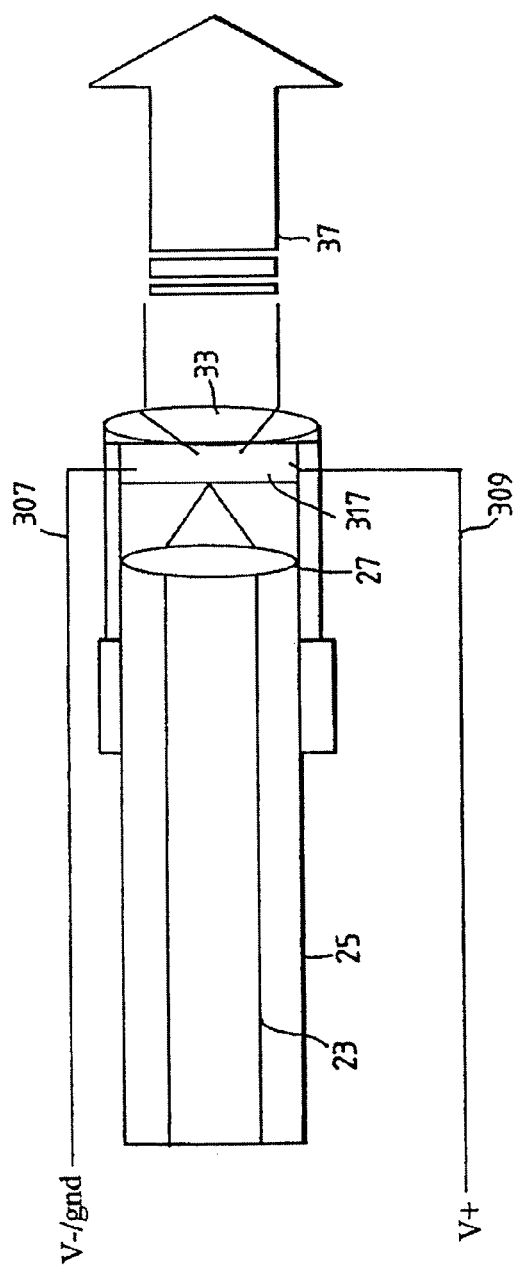
FIG. 16 shows a further variation on a THz probe in accordance with an embodiment of the present invention, where the frequency conversion member is provided by a p-i-n diode.

FIG. 16 shows a further variation on an emitter. To avoid unnecessary repetition, like reference numerals will be used to denote like features as described with reference to FIGS. 14 and 2. The probe pulse is directed through lens 27 onto p-i-n diode 317. The p-i-n diode works in a similar manner to the photo conductive emitter described with reference to FIG. 14. In an emitting mode, a bias is applied via leads 307 and 309, an application of a suitable bias results in the emission of THz beam 37 through THz lens 33. Again, this p-i-n diode can be used to function as a detector as described with reference to FIG. 15.

Figure 17:
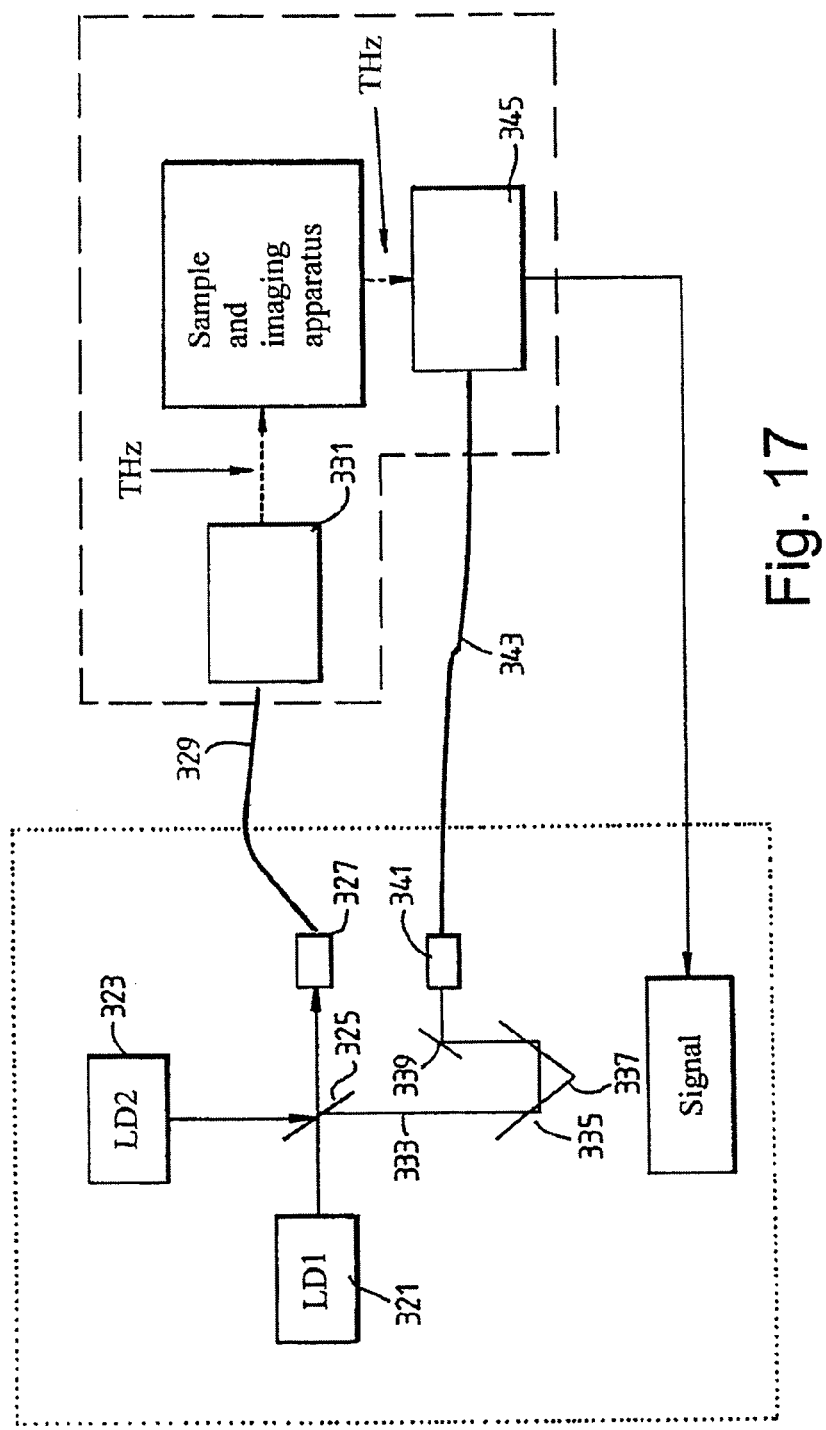
FIG. 17 shows a schematic outline of a THz emission and detection system using CW laser diodes in accordance with an embodiment of the present invention.

Previously, the operation of the probe has been specifically discussed using pulsed laser beams. However, the present invention is not limited to the use of pulsed beams. Continuos wave (CW) laser diodes are cheaper than their pulsed diode equivalents and avoid any problems which arise due to sending a pulse down a fibre optic cable. FIG. 17 shows a system which comprises two laser diodes 321, 323 which are configured to emit radiation with frequencies $\omega_1$ and $\omega_2$ respectively. The radiation emitted from both laser diodes 321 and 323 is combined using beam splitter/combiner 325. The combined radiation which contains both frequencies $\omega_1$ and $\omega_2$ is then directed into fibre optic coupler 327 which directs the emitted radiation into fibre optic cable 329. Cable 329 carries the radiation to THz source 331 for emitting THz radiation. The THz radiation is produced with a frequency of $\omega_1-\omega_2$ and THz source 331 can use any of the previous described methods such as EOS or photo conductive emitters for generating the THz radiation.

The beams emitted from laser diodes 321, 323 are taken as the probe beam 333 using beam splitter 325. This probe beam 333 will be used to give the detector information about the phase of the radiation which is emitted from the THz source 331. The probe beam is fed into optical delay line 335 which is used as the delay control means 19 explained with reference to FIG. 1.

In the optical delay line, the probe beam 333 is reflected off cube mirror 337 which is used to reflect the light through 180° and onto mirror 339 which in turn reflects the probe beam 333 into fibre optic coupler 341. Fibre optic coupler 341 directs the probe beam into fibre optic 343 and into THz detector head 345.

Improvements in the signal to noise ratio and hence acquisition times can be made by various modulation schemes. For example, dithering or oscillating of the mirror 337 will cause sinusoidal variations in the $d_p$ that can be detected using standard lock-in techniques. This is essentially a frequency modulation of the THz waveform as it is plotted out versus $d_p$. Similarly, it is possible to modulate the amplitude or frequencies of the sources outputting the radiation $\omega_1$ and $\omega_2$ to affect the amplitude and/or frequency modulation. This again results in noise suppression.

Figure 18:
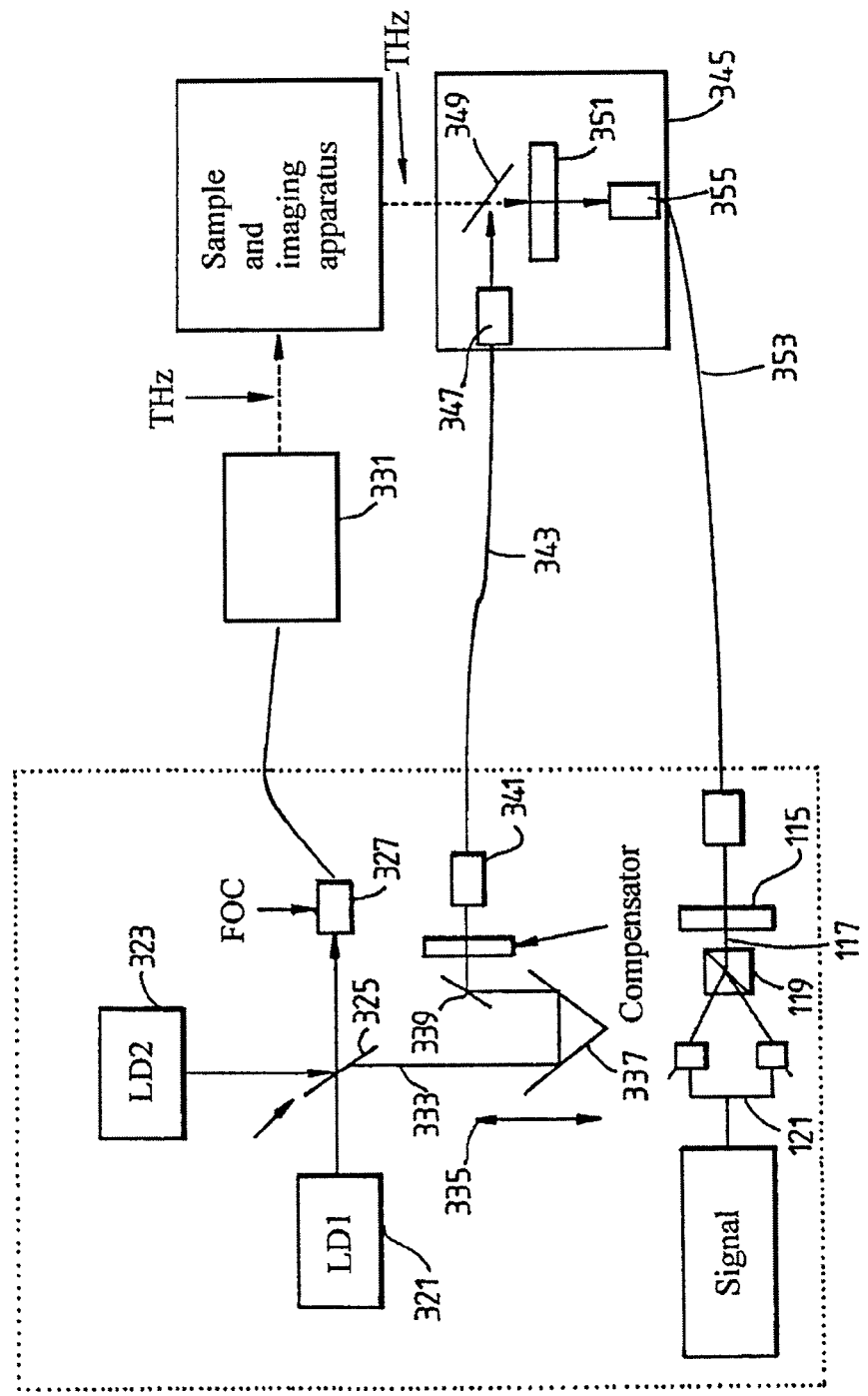
FIG. 18 shows a further variation on the system of FIG. 17.
Figure 19:
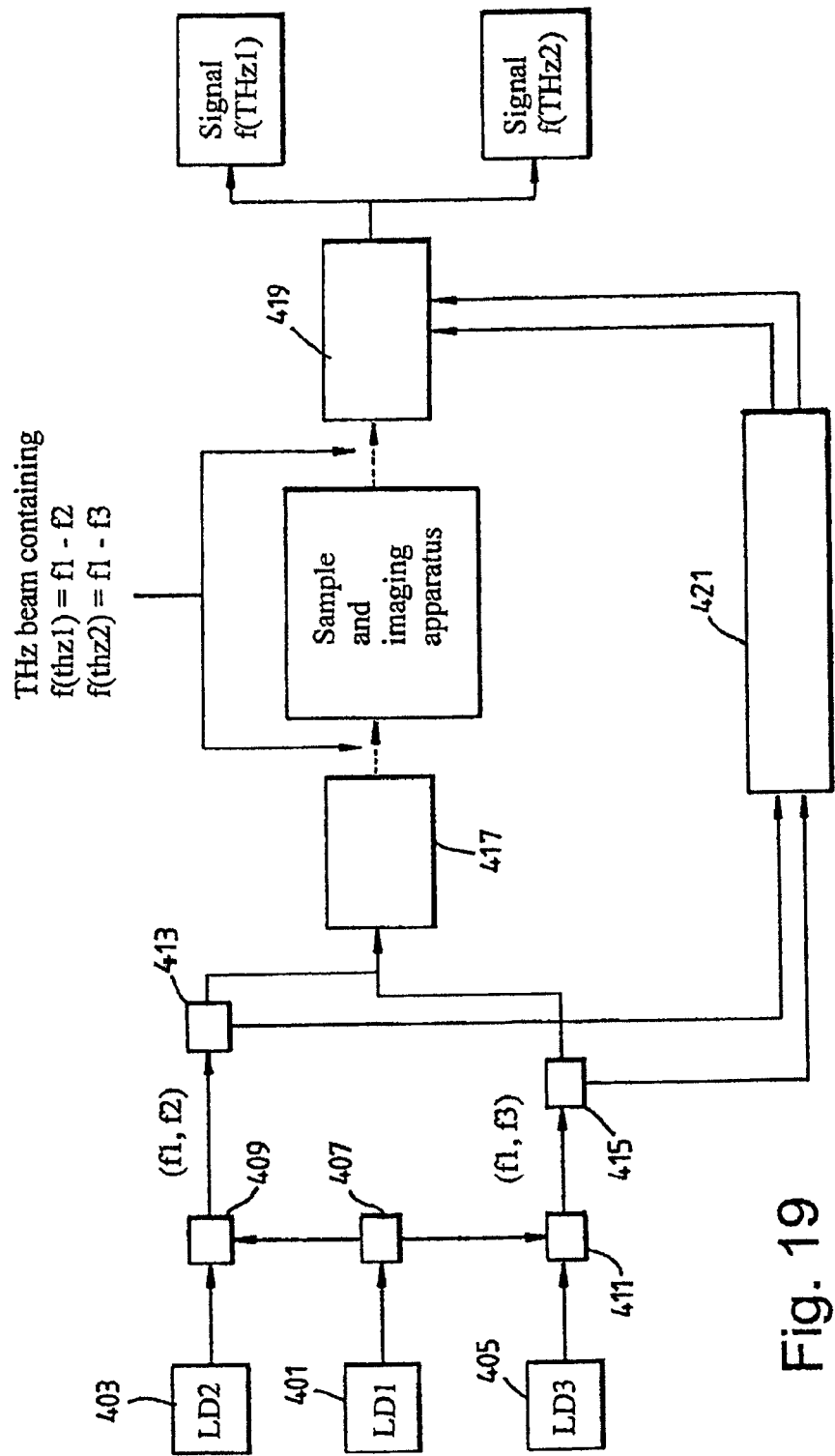
FIG. 19 shows a variation on the systems of FIGS. 17 and 18 using two THz frequencies to illuminate the sample.

FIG. 18 shows the system of FIG. 17 using EOS to detect the THz beam. To avoid unnecessary repetition, like numerals have been used to denote like features. The reference beam 343 is carried to THz detector via fibre optic cable 343. Fibre optic cable 343 is terminated by fibre optic coupler 347. The reference beam is then combined with the detected THz radiation via beam combiner 349. The combined beam is then directed into Non-linear material 351. The non-linear material is configured so that the polarisation of the reference beam is rotated in accordance with the detected THz beam. The beam with the rotated polarisation vector is then fed in fibre 353 via fibre optic couple 355.

Fibre optic cable 353 directs the radiation back to the analysis equipment. Fibre optic cable is terminated by fibre optic couples 357. This radiation is then fed into a polarisation analyser as described with reference to FIG. 10.

Here, the sample is illuminated with two frequencies in the THz range. The THz generator is based on the generator described with reference to FIGS. 3 and 4. There are three laser diodes, 401, 403 and 405. The first laser diode 401 emits radiation with a frequency $\omega_1$ into beam splitter 407. Beam splitter 407 directs part of the beam into beam combiner 409 where it combines with radiation of a frequency $\omega_2$ emitted from the second diode. The other part of the beam is directed towards combiner 411, where it is combined in beam combiner 411 with radiation from the third diode 305 having a frequency $\omega_3$.

Radiation from beam combiner 409 is directed into beam splitter 413 which in turn splits the beam into an input for the phase control means 7 and an input for the THz source 417.

Radiation from beam combiner 411 is directed into beam splitter 415 where it is split into an input for the phase control means 7 and an input to the THz source 417. The THz source is configured to output beams in the THz range with frequencies $\omega_1$-$\omega_2$ and $\omega_1$-$\omega_3$. These two beams travel through the sample 3. Typically, the two THz frequencies $\omega_1$-$\omega_2$ and $\omega_1$-$\omega_3$ will be chosen such that they can be used to probe different materials which make up the sample.

The two transmitted THz beams are combined with the two reference beams as previously described. The detector 419 can be any type of detector which has been previously described for the use of one THz beam. The different frequency components can be split by Fourier transforming the signal obtained due to the detected radiation.

Figure 20:
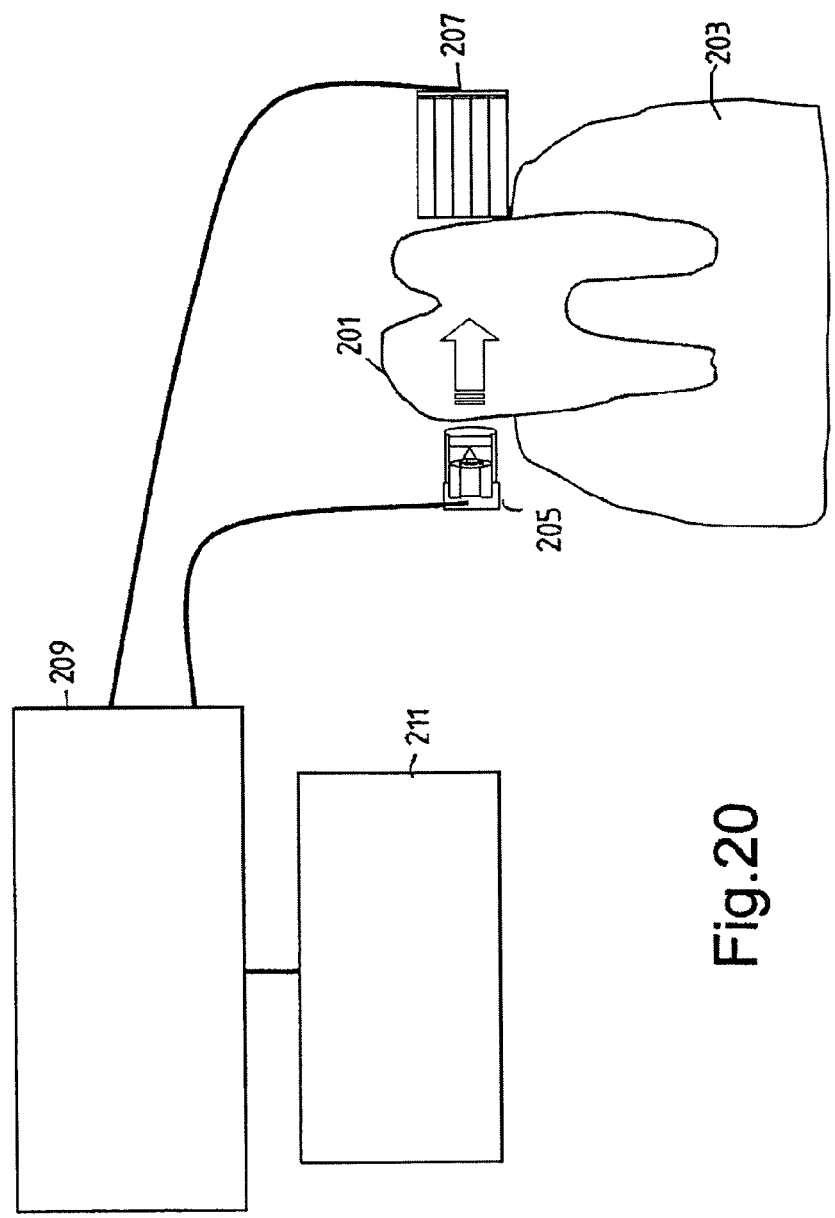
FIG. 20 shows a probe in accordance with a preferred embodiment of the first aspect of the present invention used with a tooth.

FIG. 20 shows an application of the THz probe. Here, it is used for dentistry. The sample to be imaged is a tooth 201 which is in a gum 203. An emitter 205 which may be an emitter of the type described with reference to any of FIGS. 2 to 5 and a multi-element detector head 207 is provided on the opposite side of tooth 201 to the emitter head 205. Both the emitter 205 and the detector 207 receive a pulse from laser source 209. The laser source 209 also serves to collect the data transmitted from detector 207. The laser source is then connected to imaging analysis means 211 which provides a THz image of the tooth.

The probe may also be positioned on either side of the bone below the tooth. This can be used to detect periodontal disease.

Figure 21:
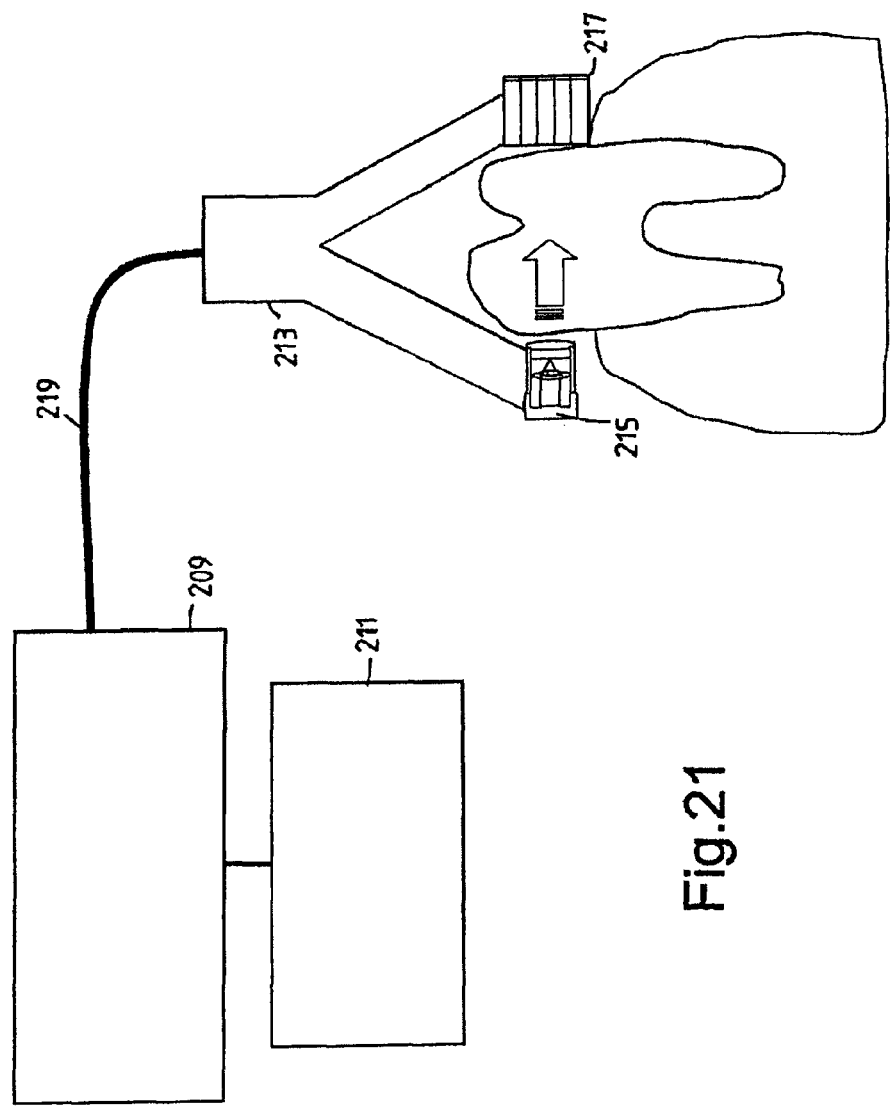
FIG. 21 shows a variation on the probe of FIG. 13 used with a tooth.

FIG. 21 shows a variation on the system of FIG. 13. A single probe 213 is provided. The single probe 213 is Y-shaped. A THz emitter 215 is provided on one of the Y and a THz detector 217 is provided on the opposing end of the Y shape. All the fibres are delivered along a single cable 219 to the probe 213. The laser source 209 and the analysis means 211 remain the same as those for FIG. 13.

Figure 22A:
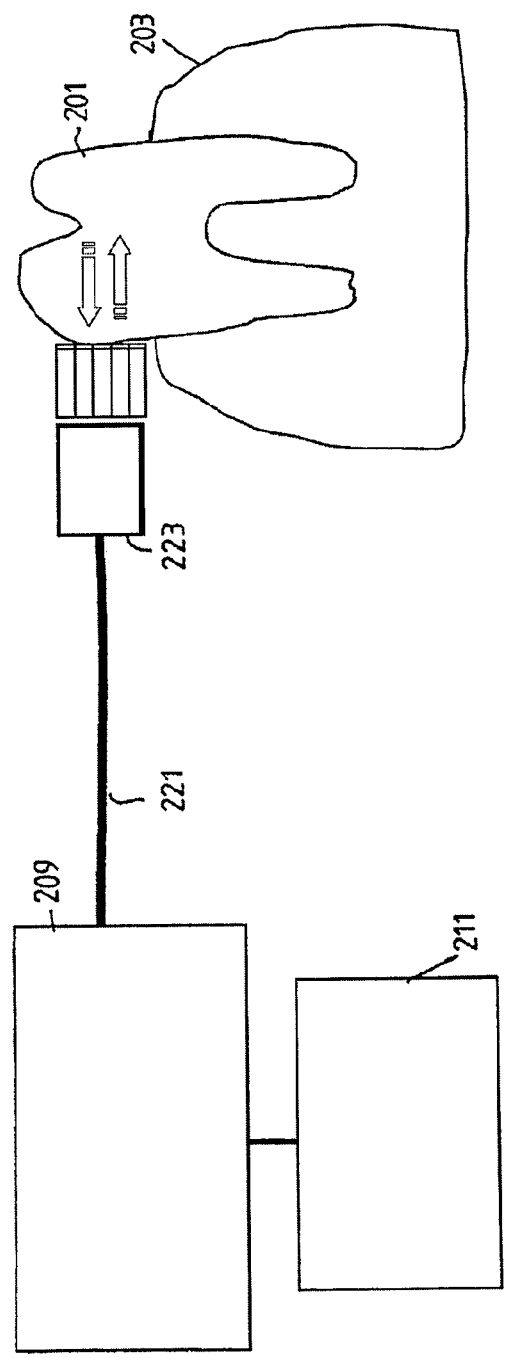
FIG. 22A shows a probe in accordance with a preferred embodiment of the first aspect of the present invention used for probing a tooth using reflection.

FIG. 22A shows a further example of the probe. Here, the probe works on reflection as opposed to transmission. As for FIGS. 20 and 21, the laser source 209 and image analysis 211 provide the same function. All signals to and from the probe are provided by a single cable 221. The probe 223 is positioned next to the tooth. The emitter and detector must sit at the same space of the probe. This could be achieved using the arrangement of FIG. 11 or that of FIG. 12.

Figure 22B:
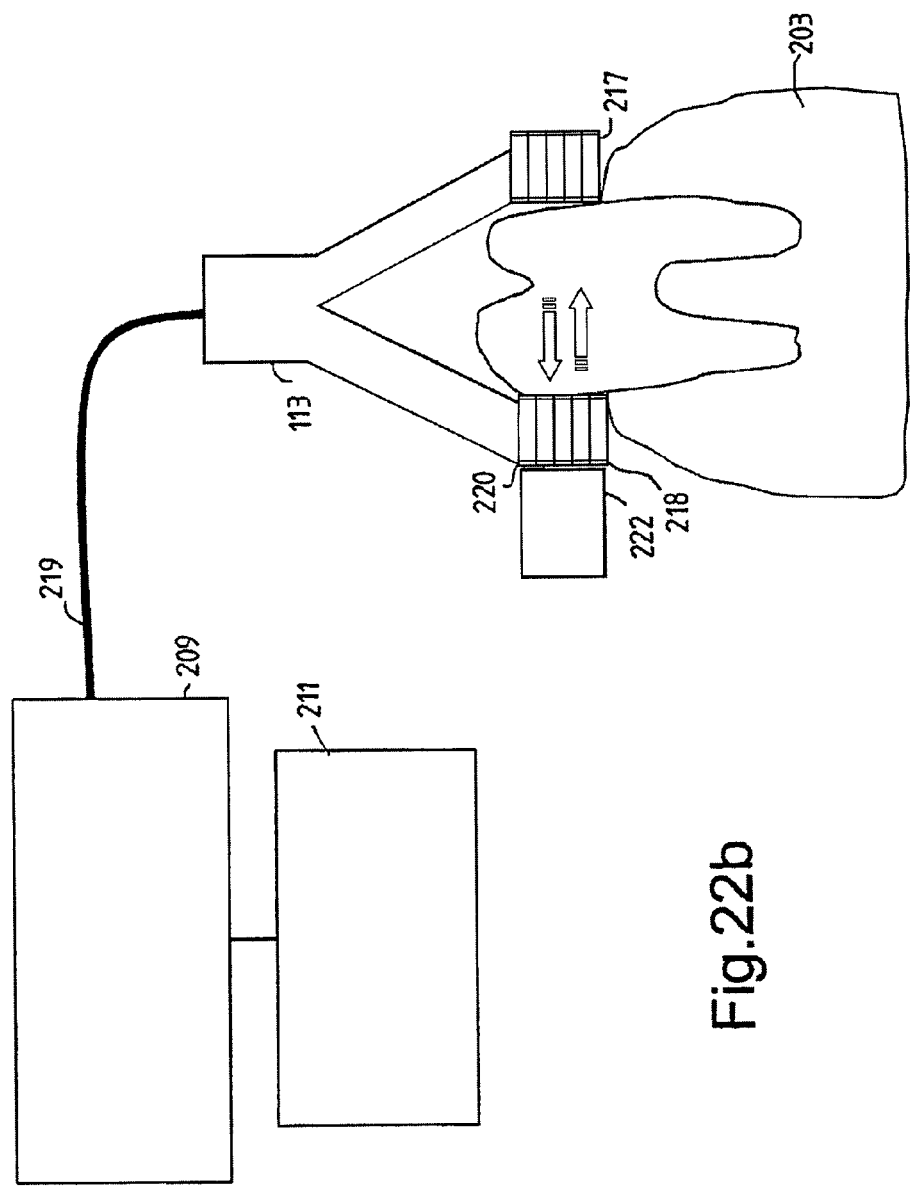
FIG. 22B shows the probe of 22A using both transmission and reflection.

FIG. 22B shows a further example of the probe. Here, the probe works on both transmission as well as reflection. The probe has the Y shape configuration of FIG. 21. To avoid repetition, the same reference numerals will be used to denote the same features. Transmission detector head 217 is provided with a plurality of detector elements. Reflection head 218 is provided with a plurality of detection elements 220 and an emitter element 222. The emitter irradiates the tooth and the section head 217 detects transmitted radiation and the detection head 218 detects reflected radiation.

FIG. 23 shows photographs and a CCD image of a tooth. FIG. 23A shows an outside view of the tooth showing the shiny enamel. FIG. 23B shows the inside of a tooth, the enamel 301 can be seen at the outside of the tooth, the dentine 303 is seen inside the enamel and the pulp cavity 305 is located in the centre of the tooth. FIG. 23C shows a CCD image of the cut tooth of FIG. 23B. Again, the enamel 301, the dentine 303 and the root cavity can be clearly distinguished.

The outside of the tooth is denoted by numeral I, the enamel will be denoted by numeral II and the dentine/root cavity will be denoted by III. The tooth in FIG. 23 is an extracted premolar with no large, obvious carious region in the main portion of the tooth. At a frequency of 0.7 THz, the absorption coefficient was estimated at 8 cm$^{-1}$ from a tooth that was roughly 9 mm thick.

Figure 24:
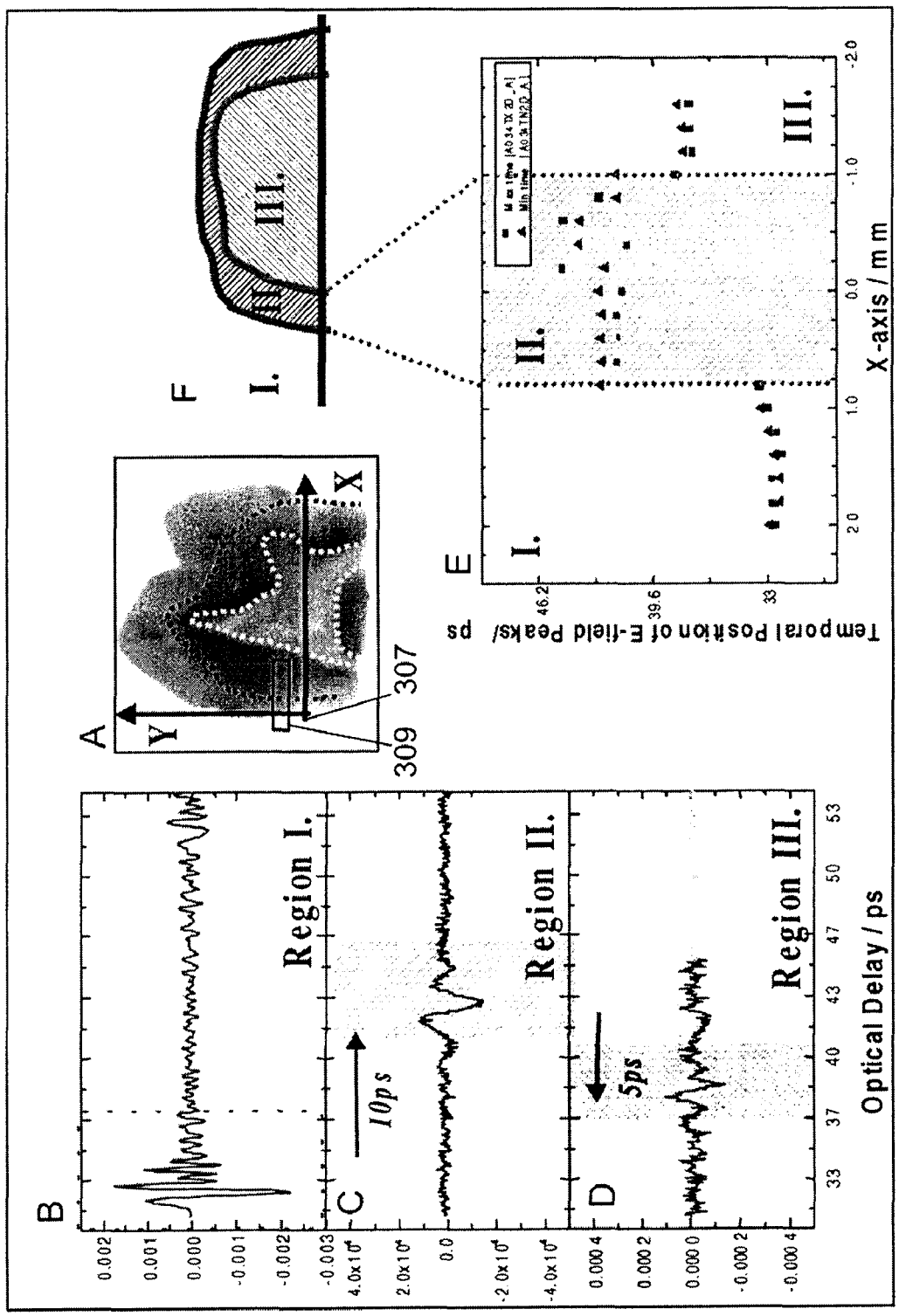

FIG. 24 is used to describe THz data taken from the tooth of FIG. 23. FIG. 24A shows the CCD scan of FIG. 23C. However, here, an axis 307 has been entered onto the figure. Also, there is a box 309 which represents the sampling area for the THz. The time of flight or delay of a THz pulse as it passes through an object of thickness d and refracted index n, relative to a reference pulse travelling through the air it is given by:

$$\text{Delay}=d(]n-1)/c$$

Hence, by measuring the delay of the THz pulse passing through an object at a speed c/n relative to a reference beam travelling at the speed of light in free space c, the thickness D can be determined to an accuracy of typically plus or minus 1 μm.

Using the above equation, it is clear that the delay or difference in the time of flight can be used to construct an image of the object. FIGS. 24B to 24D show time domain traces of the THz pulse as it passes through the three regions:
I) outside of the tooth;
II) in the enamel region; and
III) in the region covered by both enamel and dentine (please refer to FIG. 23).

The three regions were accessed by fixing the y-position on the tooth and performing a line scan in the x-direction. X and Y are defined in FIG. 24A. Moving from the outside of the tooth (1) to the inside of the enamel region (2), a delay of (10 ps) occurs as the pulse travels through the tooth enamel. As the pulse moves from the enamel region (2) into the immediately adjacent enamel and dentine region (3), a large decrease in the delay is observed (reduction to 5 ps) in spite of a very small change in overall tooth thickness. The relatively small contribution of thickness changes to a very large gap in the delay time between regions 2 and 3 as supported by the fact that the delay increases very slowly across region 3 itself where they should be little variation in the refractive index.

The data suggests a relatively large change in refractive index of THz frequencies between the enamel and dentine. This is believed to occur because the enamel is hard and therefore more likely to be denser than the dentine which would increase the refractive index. Also, there are important structural differences between the enamel and dentine. Further, the chemical composition of the two tissues is different and also results in different indices, for example enamel is about 99% mineral whereas dentine is about 70% mineral. This can also be seen in the variant shape of the pulse as shown in FIGS. 24C and 24D.

FIG. 24E is a plot of the temporal shift of measured peaks from FIGS. 24B to D plotted against position alone the x-axis 307 of box 309. The squares correspond to the maximum peak shift observed and the triangles correspond to the minimum peak shift observed. The enamel region 2 can be seen to have the largest shifts in peaks. The enamel and dentine region 3 has a much lower peak shift. FIG. 24 is a schematic cross section of the tooth. FIGS. 24F and 24E have been joined to illustrate how the THz changes throughout the path of the tooth.

Figures 25A, 25B:
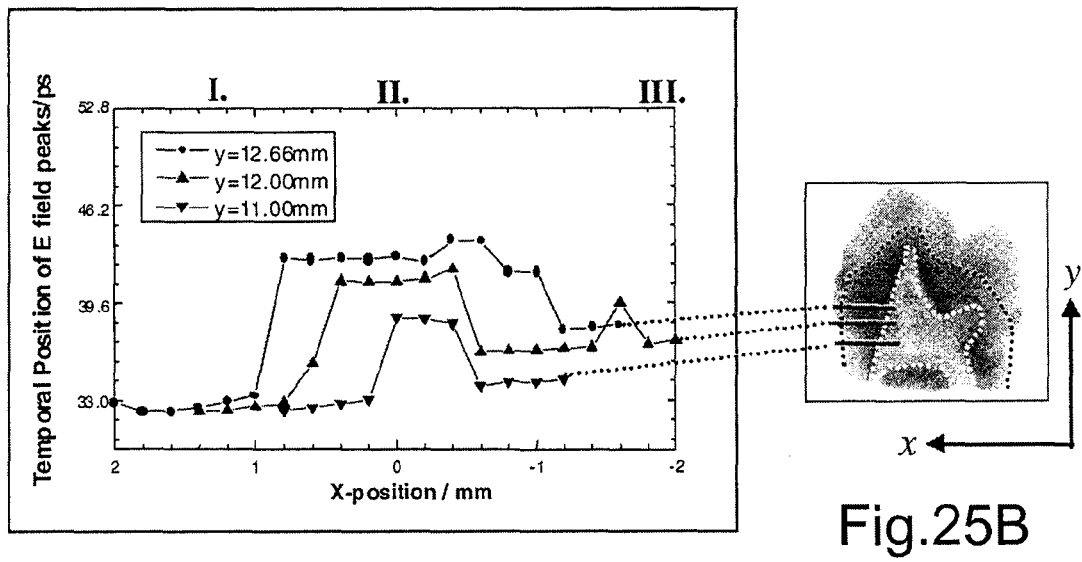
FIGS. 25A-B shows a plot of the temporal position of the peaks in a THz pulse passed through the tooth of FIG. 23.

FIG. 25A is a plot of temporal position of the peaks in the THz pulse as a function of x position in the tooth. The x-axis is shown on FIG. 25B. The same tooth is used as described in FIG. 23. The three regions outside tooth, enamel and enamel plus dentine are the same as previously described with reference to FIGS. 23 and 24. FIG. 25B shows the position of the THz scans. Three scans were taken at three different points along the y-axis (11 mm, 12 mm and 12.66 mm). For each x-line scan, a given y, the time delay of the positive going portion of the THz pulse is plotted at a function of x. As y increases, corresponding to x scans through region where the enamel is progressively thicker, the portion of the x scan dominated by long delay times (10 ps) increases. This increase reflects the larger width of the enamel as one travels from the bottom of the tooth (y) to the top of the tooth (Y).

Figure 26:
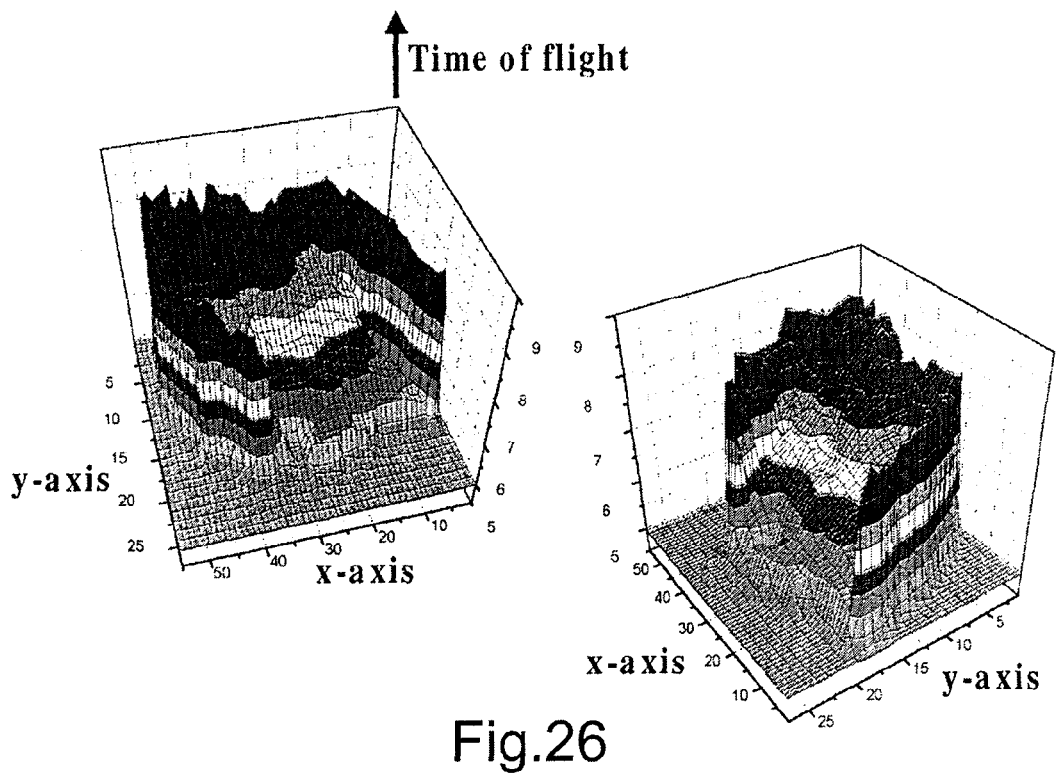
FIG. 26 shows the temporal positions of THz pulses in an x-y plane of the tooth of FIG. 23.

FIG. 26 shows the temporal positions of THz pulses in an x, y plane of the tooth.

FIG. 26 shows an area 311 which represents the sample scanning area. FIG. 26A is a plot of the temporal position of the THz pulses against x-axis. The squares correspond to the maximum time difference measured and the circles correspond to the time delay. For ease of viewing, the squares and circles on the right hand side of the picture which correspond to the boundary between the enamel and the dentine and enamel have been made smaller.

Figure 27:
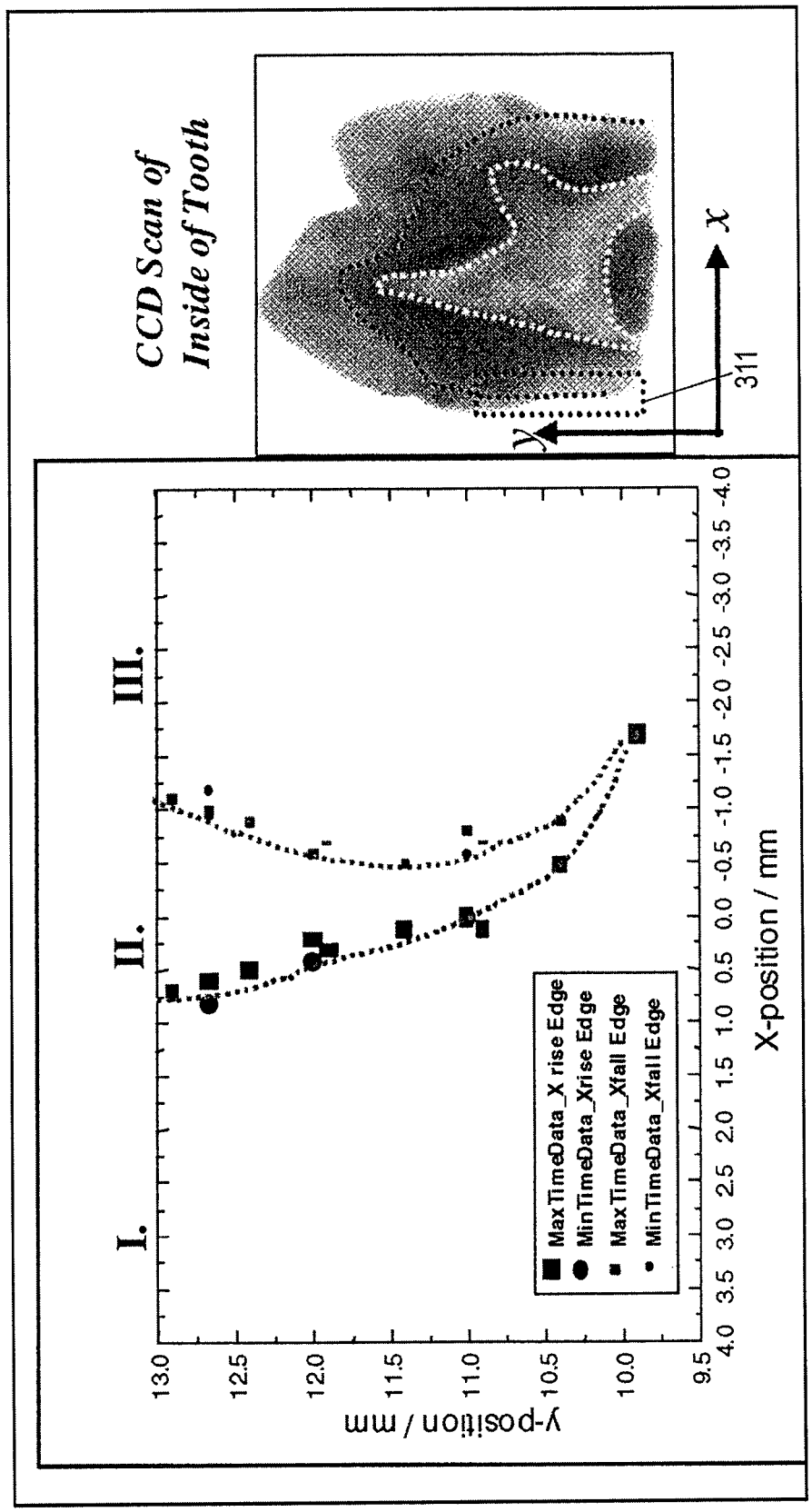
FIG. 27 shows a three dimensional plot using the data from FIGS. 17 to 19.

FIG. 27 shows a three dimensional plot using all of the data from FIGS. 24 to 26. The time delay is plotted for each pixel.

FIG. 28 shows a two dimensional contour plot of the tooth which shows that the difference between enamel only and enamel and dentine can be easily established.

FIG. 29 shows a panchromatic absorption image which shows the presence of the pulp cavity.

Figure 30A:
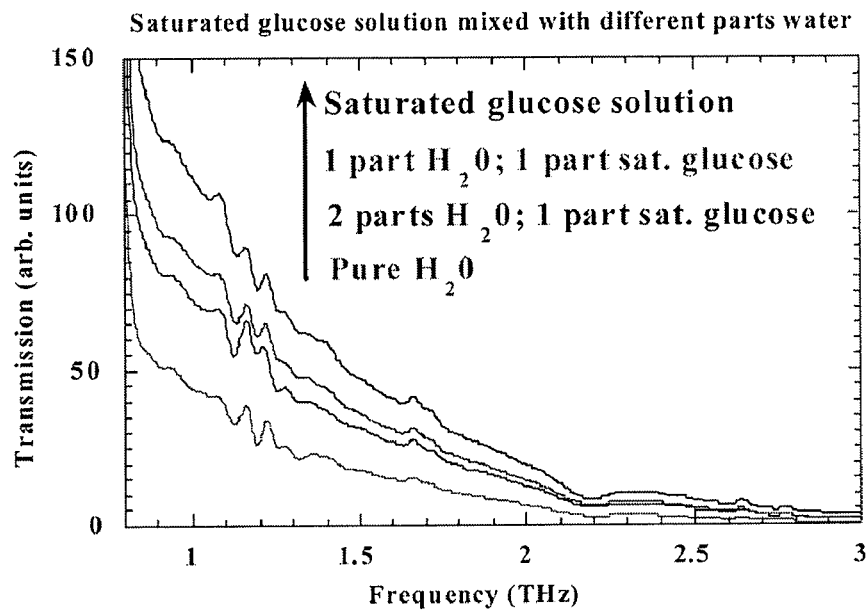
FIGS. 30A and 30B shows a plot of THz transmissions through a saturated glucose solution.
Figure 30B:
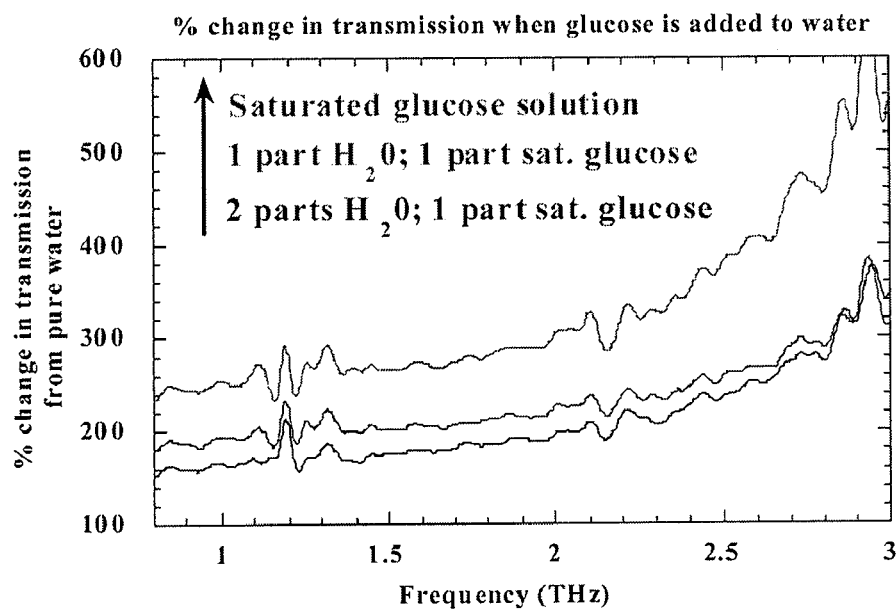

FIGS. 30A and 30B shows a plot of THz transmission through a saturated glucose solution mixed with different parts of water. The upper trace refers to saturated glucose solution. The lower trace is pure water. It can be seen that the absorption of the THz signal decreases as the glucose concentration is increased. FIG. 30B shows the data of FIG. 30A plotted as a percentage change in transmission from pure water.

In advanced cases of caries, due to the inversion of bacteria, a dentine caries solution changes its chemical composition quite dramatically. Exclusion of water by micro-organisms, sugar or acid will lead to changes in the integrated absorption spectrum across the frequency range. This is clearly evidenced by FIG. 30. Thus, FIG. 30 shows the power of using THz to examine teeth.

Figure 31:
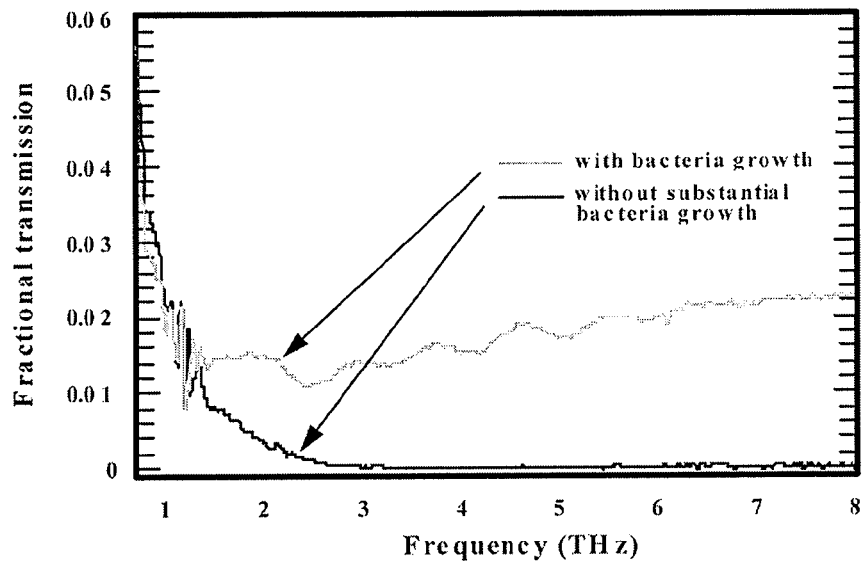
FIG. 31 is a plot of THz transmission against frequency of a new born calf serum.

FIG. 31 is a plot of transmission of THz signal across frequency of a new born calf serum. The lower trace shows the serum with bacteria growth. The upper trace shows the serum with no bacterial growth.

This figure shows the growth of bacteria and other organisms in this serum significantly change the THz absorption. It is expected that the introduction of bacteria into teeth would also show such a similar transmission which can be detected by THz.

Figure 32:
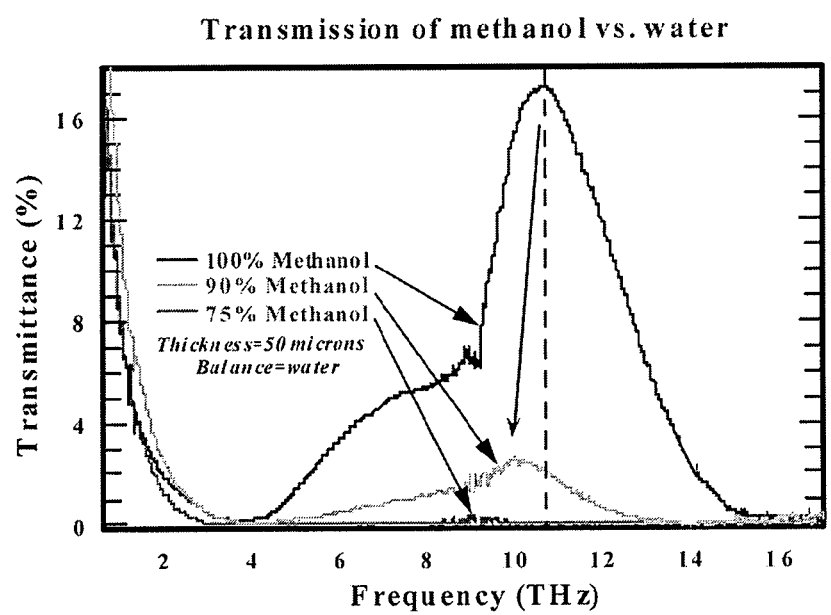
FIG. 32 shows a further plot of transmission of THz against frequency through a methanol solution.

FIG. 32 shows a further plot of transmission of THz against frequency. This time, the solution is methanol and water is progressively added. As water is added to the solution, the transmission through the sample decreases.

FIG. 33 shows a plot of THz transmission against frequency for clotted blood. The upper trace is the reference, the lower trace is 90 μm of clotted blood. The clotted blood is seen to have a higher absorption than that of the reference.

FIG. 34 shows THz being used to image different types of animal tissue. Here, it is used to image bone. The ability to image bone composition clearly shows that THz can be used to image periodontal disease which manifests itself in loss of bone from below the tooth.

The invention claimed is:

1. A probe assembly for examining a sample, the assembly comprising:
a probe;
a fibre optic cable for communicating signals to and/or from the probe;
an emitter for emitting radiation to irradiate the sample, the emitter being located in the probe; and
an electro-magnetic radiation detector for detecting radiation which is transmitted through or reflected from the sample,
the emitter comprising a frequency conversion member which emits radiation having at least one frequency in the range 0.1 THz to 84 THz in response to being irradiated with input radiation which has a different frequency to that of the emitted radiation, wherein the frequency conversion member comprises a photoconductive emitter, wherein the fibre optic cable communicates the input radiation to the probe.

2. The probe assembly of claim 1, wherein both the emitter and detector are located in the probe.

3. The probe assembly of claim 1, wherein the emitter is located within the probe and the fibre optic cable supply the emitter with the input radiation to irradiate the frequency conversion member.

4. The probe assembly of claim 3, wherein the input radiation comprises at least one pulsed beam of radiation.

5. The probe assembly of claim 3, wherein the input radiation comprises at least one beam of substantially continuous radiation.

6. The probe assembly of claim 1, wherein the emitter is configured to emit a plurality of frequencies in the range from 0.1 THz to 84 THz.

7. The probe assembly of claim 1, wherein the frequency conversion member comprises an optically non-linear member.

8. The probe assembly of claim 7, wherein the frequency conversion member comprises at least one of the following: LiI03, NH4H2PO4, ADP, KH2PO4, KH2ASO4, Quartz, A11304, ZnO, CdS, GaP, GaAs, BaTO3, LiTaO3, LiNbO3, Te, Se, ZnTe, ZnSe, Ba2NaNb5O15, AgAsS3, proustite, CdSe, CdGeAs2, AgGaSe2, AgSbS3, ZnS, DAST (4-N-methylstilbazolium) or Si.

9. The probe assembly of claim 1, wherein the frequency conversion member is provided with phase matching means configured to match the phase of radiation of at least one beat frequency of the input radiation and the emitted radiation at all points within the frequency conversion member.

10. The probe assembly of claim 1, wherein the photo conductive emitter comprises low temperature GaAs, semi-insulating GaAs, silicon on Sapphire, semi-insulating InGaAs, low temperature InGaAs, semi-insulating InP or As implanted GaAs.

11. The probe assembly of claim 1, wherein the frequency conversion member has a p-i-n structure.

12. The probe assembly of claim 1, wherein the fibre optic cable comprises at least two sections wherein one section has a positive dispersion effect and another section has a negative dispersion effect on the radiation being carried by the cable.

13. The probe assembly of claim 1, wherein the probe is provided with dispersion shifting means which provide a negative dispersion effect.

14. The probe assembly of claim 1, wherein the detector comprises a non-linear crystal.

15. The probe assembly of claim 1 wherein the detector member comprises at least one of: LiI03, NI-14142PO4, ADP, KH2PO4, KH2ASO4, Quartz, AlPO4, ZnO, CdS, GaP, GaAs, BaTiO3, LiTaO3, LiNbO3, Te, Se, ZnTe, ZnSe, Ba2NaNb5O15, AgAsS3, proustite, CdSe, CdGeAs2, AgGaSe2, AgSbS3, ZnS, DAST (4-N-methylstilbazolium) or Si.

16. The probe assembly of claim 1, wherein the detector comprises an photo conductive detector.

17. The probe assembly of claim 16, wherein the photo conductive detector comprises low temperature GaAs, semi-insulating GaAs, silicon on Sapphire, semi-insulating InGaAs, low temperature InGaAs, semi-insulating InP or As implanted GaAs.

18. The probe assembly of claim 16, wherein the photo conductive detector comprises a p-i-n structure.

19. The probe assembly of claim 1, wherein when the detector is located in the probe and information from the detected radiation is transmitted out of the probe by radiation with a different wavelength to that of the detected radiation.

20. The probe assembly of claim 19, wherein the radiation is polarised before it is transmitted out of the probe.

21. The probe assembly of claim 1, wherein information in the detected radiation is transferred to radiation of a different frequency to that of the detected radiation, the radiation being supplied to the detector by a detector radiation supply means.

22. The probe assembly of claim 1, wherein a CCD array is provided within the probe.

23. The probe assembly of claim 1, wherein the probe is configured to be inserted into a human or animal body.

24. The probe assembly of claim 1, wherein the probe is configured for use in key hole surgery.

25. The probe assembly of claim 1, wherein the width of the probe is at most 10 mm.

26. The probe assembly of claim 1, further comprising imaging means for producing an image of the sample.

27. The probe assembly of claim 1, further comprising compositional analysing means for determining information about the composition of the sample from the detected radiation.

28. The probe assembly of claim 1, wherein the probe is provided with tooth clamping means.

* * * * *